(12) United States Patent
Nishimura et al.

(10) Patent No.: US 7,790,957 B2
(45) Date of Patent: Sep. 7, 2010

(54) GENES THAT CONFER REGENERATION ABILITY TO PLANTS, AND USES THEREOF

(75) Inventors: Asuka Nishimura, Saitama (JP);
Makoto Matsuoka, Nagoya (JP);
Motoyuki Ashikari, Nagoya (JP)

(73) Assignees: Honda Motor Co., Ltd., Tokyo (JP);
National University Corporation Nagoya University, Aichi (JP)

( * ) Notice: Subject to any disclaimer, the term of this patent is extended or adjusted under 35 U.S.C. 154(b) by 751 days.

(21) Appl. No.: 10/566,593

(22) PCT Filed: Jul. 30, 2004

(86) PCT No.: PCT/JP2004/011307

§ 371 (c)(1),
(2), (4) Date: Aug. 17, 2006

(87) PCT Pub. No.: WO2005/012520

PCT Pub. Date: Feb. 10, 2005

(65) Prior Publication Data

US 2007/0186302 A1 Aug. 9, 2007

Related U.S. Application Data

(60) Provisional application No. 60/491,837, filed on Jul. 31, 2003.

(51) Int. Cl.
*A01H 1/00* (2006.01)
*C07H 21/04* (2006.01)
*C07K 14/415* (2006.01)
*C12N 15/00* (2006.01)

(52) U.S. Cl. ............... 800/295; 435/6; 435/468; 435/419; 435/320.1; 435/183; 530/370; 536/23.1; 536/23.6; 800/278

(58) Field of Classification Search ............... None
See application file for complete search history.

(56) References Cited

FOREIGN PATENT DOCUMENTS

WO WO-01/25454 A2 4/2001
WO WO-02/36786 A2 5/2002

OTHER PUBLICATIONS

Nishimura, Asuka et al., "Isolation of a rice regeneration quantitative trait loci gene and its application to transformation systems," *PNAS*, vol. 102(33):11940-11944 (2005).
Ogawa, T. et al., "Relationships between nitrite reductase activity and genotype-dependent callus growth in rice cell cultures," *Plant Cell Reports*, vol. 18:576-581 (1999).
European Search Report for Application No. 04771310.2-2401, dated Nov. 8, 2006.
Taguchi-Shiobara, Fumio, "Genetic Analysis of Regeneration Ability of Rice Seed Callus," *Bull. Natl. Inst. Agrobiol.*, vol. 13:97-134 (1999).
Taguchi-Shiobara, F. et al, "Mapping quantitative trait loci associated with regeneration ability of seed callus in rice, *Otyza sativa* L.," *Theor. Appl. Genet.*, vol. 95:828-833 (1997).
Terada, Yoshinobu et al, "Cloning and Nucleotide Sequence of a Leaf Ferredoxin—Nitrite Reductase cDNA of Rice," *Biosci. Biotech. Biochem.*, vol. 59(11):2183-2185 (1995).
Toshinori, Abe, "Ine no Datsubunka Saibunka no Ideneki SHihai," Heisei 5, 6 Nendo Kagaku Kenkyuhi Hojokin (Sogokenkyu A), Kenkyu Seika Hokokusho, pp. 32-38 (1995).
Shiobara, Fumio, "Koshihikari ni Takai Callus Keiseino Oyobi Saibunkano o Fuyo suru Tameno QTL Kaiseki," Seibutsu Shigen Kenkyu Seika Joho, vol. 7:45-46 (1998).
Taguchi, Fumio et al, "Ine Shushi Callus no Saibunkano ni Kanyo suru QTL no Mapping," Breeding Science, vol. 46, Bessatsu 1, p. 77 (1996).
International Search Report for Application No. PCT/JP2004/011307, dated Nov. 30, 2004.
International Preliminary Report on Patentability for Application No. PCT/JP2004/011307.
Ozawa, Kenjiro et al, "Ine Saibunkano no Iden Kaiseki Oyobi Kosaibunkano Ikushu Sozai no Kaihatsu," retrieved online at http://www.nias.affrc.go.jp/seika/nias/h14/index.html (May 2003).

*Primary Examiner*—Phuong T Bui
(74) *Attorney, Agent, or Firm*—Lahive & Cockfield, LLP; Jeanne M. DiGiorgio, Esq.

(57) ABSTRACT

A gene relating to the regeneration ability of plants was successfully isolated and identified using linkage analysis. Furthermore, methods for breeding highly regenerative varieties, methods for transforming uncultulable varieties, and methods for selecting transformed cells, wherein these methods utilize this gene, were also discovered. The present invention is useful in fields such as cultivar improvement and gene analysis that uses transformation methods.

18 Claims, 9 Drawing Sheets

VECTOR　　　　　　3F

+NaNO₂ a b

GUS - Stained a  b

GENES THAT CONFER REGENERATION ABILITY TO PLANTS, AND USES THEREOF

RELATED APPLICATIONS

This application is a 35 U.S.C. 371 national stage filing of International Application No. PCT/JP2004/011307, filed 30 Jul. 2004, which claims priority to U.S. Provisional Patent Application No. 60/491,837, filed 31 Jul. 2003, the entire contents of each of which is hereby incorporated by reference.

TECHNICAL FIELD

The present invention relates to the isolation and identification of genes that confer regenerative ability to plants, as well as methods for increasing regeneration ability and methods for selecting transformed cells, where these methods utilize these genes. The present invention allows improvement of the culture characteristics of plants, and development of transformation methods with special consideration to safety.

BACKGROUND ART

Under appropriate conditions, differentiated plant tissues dedifferentiate and form calli (groups of dedifferentiated cells) after undergoing cell divisions. Depending on the conditions, calli can further redifferentiate to regenerate complete plant bodies. The ability of such differentiated cells or dedifferentiated cells to regenerate individual bodies is called totipotency, and this was initially demonstrated in the 1930s to 1950s in cultivation studies of tobacco, tomatoes, and such. Tissue culture techniques are based on this totipotency, and have been widely utilized, particularly in the field of plant breeding. For example, tissue culture techniques have been used in the production of new varieties by cell fusion and ovule culture, shortening the number of years taken for breeding and fixing of hereditary character. In recent years, tissue culture techniques have become essential for molecular breeding and basic research on plants as key techniques in artificial gene transfer (transformation methods) aimed at the functional analysis of genes.

Totipotency is generally thought to be an ability possessed by all plants. In fact, depending on the plant type, variety or organ, it is known to be easy for some plants to exhibit this ability, and difficult for others. Compared to dicotyledonous plants, the tissue culture and regeneration of monocotyledonous plants including major crops such as rice, wheat, and corn is difficult, and therefore repeated trial and error is necessary for analyses involving cultivation, including transformation methods. In rice a relatively simple culturing system has been established using the ripe seeds of specific varieties, however varieties with sufficient regenerative ability are limited. In particular, palatable varieties such as Koshihikari and Sasanishiki, and the IR line varieties widely cultivated in the tropics have low regenerative abilities, and regeneration of a plant body by tissue culturing is difficult. Improving the regenerative ability of these varieties would not only be useful for selective breeding and study of gene characteristics, but might also lead to elucidation of the mechanism of the regenerative process. In addition, the regenerative ability of other unculturable plant species and varieties might also be improved.

Furthermore, in recent years a large number of genetically modified agricultural products (GMOs) have been developed, and their planted area is increasing year by year. At the same time, many consumers are worried about their safety. The major concern in discussions on the safety of GMOs is their incorporation of antibiotic-resistance genes. Therefore, development of transformation methods that do not use antibiotic-resistance genes will ease existing consumer concern over GMOs, and at the same time may also be advantageous to researchers as simple transformation methods that do not require expensive antibiotics.

DISCLOSURE OF THE INVENTION

Regeneration ability is governed by the interaction of a number of genes as a quantitative trait (QTL: quantitative trait locus), but to date there have been no reports of the successful isolation of regenerative ability genes from that gene locus. An objective of the present invention is to isolate and identify genes involved with the regenerative ability of plants, and to provide methods for improving plants by utilizing these genes, and transformation methods utilizing these genes as selection markers.

Prior to breeding a hybrid population for use in detecting regenerative ability QTLs, the present inventors selected varieties to be parents of the hybrid population. They selected two varieties with a clear difference in regenerative abilities: japonica rice "Koshihikari" and indica rice "Kasalath" (photograph FIG. 1). F1 individuals were produced by crossing these two cultivars, and these were then backcrossed using Koshihikari as the recurrent parent, and self-fertilized. 99 lines of a BC1F1 population were produced, and BC1F2 seeds were collected. After using 20 BC1F2 seeds of each line to culture calli in an induction medium for 30 days, the grown calli were transferred to a regeneration medium, and this was cultivated for a further 30 days. After the 30 days, callus weight and the number of shoots per seed were measured, and average values were determined using 20 seeds of each line. This was taken to be the regenerative ability (graph FIG. 1). Genotyping of each line was carried out using 262 PCR markers. When QTL analyses relating to regenerative ability were carried out based on these data, four QTLs with the effect of increasing regenerative ability were found (FIG. 2). It was successfully found that in one of these QTLs near the TGS2451 marker on the short arm of chromosome 1 (PSR1; Promoter of shoot Regeneration 1), the Kasalath genome had a large increasing effect on the regenerative ability of Koshihikari (FIG. 2). Next, to identify the approximate locus of the PSR1 gene, 30 individuals whose PSR1 region had been substituted with that of Kasalath were selected from the BC2F1 population, and calli were induced using ten seeds (BC2F2 seeds) from each of these individuals. DNAs were extracted from grown calli to determine the genotype using molecular markers, and linkage analyses were carried out by investigating regenerative ability. Furthermore, to specify the locus in detail, approximately 3,800 BC3F2 seeds in which PSR1 segregated were used to investigate genotype using molecular markers, and high resolution linkage analysis was performed. As a result, PSR1 was found to be located in an about 50.8 kb region between molecular markers 3132 and P182 (FIG. 3). Predictions of the genes in this region suggested the presence of four genes, including a hypothetical protein. To determine which of these genes are regenerative ability genes, a Kasalath BAC library (average length 120 kb) was constructed, and a BAC clone comprising a PSR1 region (BHAL15) was isolated by PCR screening. Suitable restriction enzyme sites in the BHAL15 clone were used to prepare Kasalath genome fragments comprising each candidate gene region, and these were introduced to Koshihikari. As a result, it was found that the regenerative ability of Koshihikari increased only when the Kasalath genome fragment (3F in FIG. 3) comprising the gene expected to encode ferredoxin nitrite reductase (NiR) was introduced (FIG. 4). Ferredoxin nitrite reductase is a nitrite reductase that functions using ferredoxin as the electron donor, and has the action of converting nitrite into ammonia. The nucleotide sequences of the genetic region expected to be the ferredoxin nitrite reductase gene, and approximately 2 kb upstream thereof were determined and compared for Kasalath and Koshihikari, and many mutations were found in the nucleotide sequences (FIG. 5). Furthermore, when the expression levels of the mRNA of this gene in the calli were examined by semi-quantitative RT-PCR and real-time quantitative PCR, the amount of mRNA in Kasalath was approximately 2.5 times that in Koshihikari (top and middle rows of the photographs on the left, and the graph on the right in FIG. 6). Western blot analysis using antibodies specific to the NiR protein also showed that the NiR protein is stored in larger amounts in Kasalath than in Koshihikari (bottom row of the photographs on the left in FIG. 6). Furthermore, in a comparison of NiR enzyme activity per unit protein using the naphthyl ethylenediamine method and an NiR recombinant protein expressed in *E. coli*, the Kasalath NiR showed enzyme activity approximately 1.6 times higher than that of Koshihikari (FIG. 7). The above-mentioned results showed that the difference in regenerative ability between Koshihikari and Kasalath is primarily due to differences in the level of transcriptional regulation of the NiR gene, and is secondly due to differences in activity per molecule of the synthesized protein.

Introducing the genomic region of the Kasalath PSR1 gene into Koshihikari confers regeneration ability to Koshihikari, which does not regenerate. This suggests that the Kasalath PSR1 gene can be used as a selection marker when transforming Koshihikari. More specifically, when a vector in which the Kasalath PSR1 gene and a target gene have been inserted in parallel is introduced into Koshihikari, only those cells to which the PSR1 gene has been introduced will acquire regeneration ability, and therefore regenerated plant bodies should have incorporated the target gene at the same time. To prove this notion, vectors carrying the Kasalath NiR genome+35S promoter GUS, Kasalath NiR promoter::NiR cDNA::NiR terminator+35S promoter GUS, rice Actin1 promoter::NiR cDNA::NiR terminator+35S promoter GUS in the T-DNA region of the pBI101 binary vector, and a vector that does not carry the NiR gene were constructed and introduced into Koshihikari. When three types of vectors comprising the NiR gene were introduced, many regenerated individuals were obtained in all cases, and staining due to the GUS gene was observed in the calli from which they were derived (FIG. 8). In addition, the NiR gene has the property of metabolizing nitrite, which is toxic to plants, and utilizing this characteristic also allows the NiR gene to be used as a marker for transformation of highly regenerative varieties. More specifically, a vector that overexpresses the NiR gene under the control of an actin promoter, which is a high expression promoter in rice, was introduced into a highly regenerative Kasalath variety, and this was cultured on a medium supplemented with nitrite at a concentration that would inhibit the growth of ordinary wild types. Only transformed cells grew due to the effect of the overexpressed NiR gene, and GUS staining was observed only in these grown cells (FIG. 9). The use of this selection method enabled production of safer recombinant plants without the use of antibiotic resistance genes derived from microorganisms (selection markers for transformed cells), which has been considered problematic in conventional genetically modified agricultural products. Furthermore, since expensive antibiotics were unnecessary, the cost of developing the transformants was reduced.

More specifically, the present invention relates to the isolation and identification of genes that increase the regenerative ability of plants, and improvement of the cultivation characteristics of plants by utilizing these genes, and methods of transformation that use these genes as a selection marker. The present invention provides [1] to [22], described below:

[1] a DNA involved in the regeneration ability of plants, wherein the DNA is any one of (a) to (d):

(a) a DNA encoding a protein comprising the amino acid sequence of SEQ ID NO: 3;

(b) a DNA comprising a coding region of the nucleotide sequence of SEQ ID NO: 1 or 2;

(c) a DNA encoding a protein comprising an amino acid sequence with one or more amino acid substitutions, deletions, additions, and/or insertions in the amino acid sequence of SEQ ID NO: 3; and (d) a DNA that hybridizes under stringent conditions with a DNA comprising the nucleotide sequence of SEQ ID NO: 1 or 2;

[2] a DNA encoding a partial peptide of a protein comprising the amino acid sequence of SEQ ID NO: 3;

[3] a DNA comprising a promoter region of the nucleotide sequence of SEQ ID: 1 or 2;

[4] a vector comprising the DNA of [1] or [2];

[5] a vector comprising the DNA of [3];

[6] a host cell carrying the vector of [4];

[7] a plant cell carrying the vector of [4];

[8] a plant transformant comprising the plant cell of [7];

[9] a plant transformant that is a progeny or a clone of the plant transformant of [8];

[10] a propagation material of the plant transformant of [8] or [9];

[11] a method for producing a plant transformant, wherein the method comprises the steps of introducing the DNA of [1] or [2] into a plant cell, and regenerating a plant from said plant cell;

[12] a protein encoded by the DNA of [1] or [2];

[13] a method for producing the protein of [12], wherein the method comprises the steps of culturing the host cell of [6], and collecting a recombinant protein from said cell or the culture supernatant thereof;

[14] an antibody that binds to the protein of [12];

[15] a polynucleotide comprising at least 15 continuous nucleotides that are complementary to the nucleotide sequence of SEQ ID NO: 1 or 2, or a sequence complementary thereto;

[16] a method for increasing the regeneration ability of a plant, wherein the method comprises the step of expressing the DNA of [1] or [2] in a cell of a plant;

[17] an agent for altering the regeneration ability of a plant, wherein the agent comprises the DNA of [1] or [2], or the vector of [4] as an active ingredient;

[18] a method for determining the regeneration ability of a plant cell, wherein the method comprises the step of detecting the expression of the DNA of [1] or the protein of [12] in the plant cell;

[19] a method for determining the regeneration ability of a plant cell, wherein the method comprises the step of detecting the activity of the protein of [12] in the plant cell;

[20] a method for improving the regeneration ability of a plant, wherein the method comprises the step of regulating the activity of the endogenous protein of [12] in the plant;

[21] a method for selecting a transformed plant cell, wherein the method comprises the steps of:

(a) introducing a plant cell with a vector comprising the DNA of [1] or [2] as a selection marker; and (b) culturing the plant cell and selecting plant cells that have acquired regeneration ability; and

[22] a method for altering the regeneration ability of a plant, wherein the method comprises the step of substituting the endogenous DNA of [1] or [2] in a plant by crossing.

The present invention provides DNAs that encode rice-derived NiR protein. The nucleotide sequence of the genomic DNA of "Kasalath" is shown in SEQ ID NO: 1, the nucleotide sequence of the cDNA of "Kasalath" is shown in SEQ ID NO: 2, and the amino acid sequence of the protein encoded by the DNA is shown in SEQ ID NO: 3. The nucleotide sequence of the genomic DNA of "Koshihikari" is shown in SEQ ID NO: 4, the nucleotide sequence of the cDNA of "Koshihikari" is shown in SEQ ID NO: 5, and the amino acid sequence of the protein encoded by the DNA is shown in SEQ ID NO: 6.

The present invention showed that the regenerative ability of plants can be increased by regulating the expression or activity of the PSR1 gene in plants. This enables culturing of unculturable varieties, such as Koshihikari, and enables production of stable and highly regenerative varieties.

The phrase "increase in regenerative ability" in the present invention means only that the ability of plants to regenerate under culturing conditions is increased, and the form of the regenerated individual is unchanged. This increase in regenerative ability allows the desired variety to be subjected to various cultivation experiments, and as a result, allows the efficient development of new varieties and functional analyses of genes.

In the present invention, the phrase "PSR1 gene of plants" refers to the NiR gene encoding ferredoxin nitrite reductase of plants. "PSR1 gene of plants" comprises the rice PSR1 gene (FIG. 5), and PSR1 genes derived from other plants. DNAs encoding the PSR1 protein of the present invention include genomic DNAs, cDNAs, and chemically synthesized DNAs. Genomic DNAs and cDNAs can be prepared according to conventional methods known to those skilled in the art. More specifically, genomic DNAs can be prepared, for example, as follows: (1) extract genomic DNAs from rice varieties with the PSR1 gene (e.g. Koshihikari); (2) construct a genomic library (utilizing a vector such as a plasmid, phage, cosmid, BAC, and PAC); (3) develop the library; and (4) conduct colony hybridization or plaque hybridization using a probe prepared based on a DNA encoding a protein of the present invention (e.g. SEQ ID NO: 1 or 2). Alternatively, a genomic DNA can be prepared by PCR, using primers specific to a DNA encoding a protein of the present invention (e.g. SEQ ID NO: 1 or 2). On the other hand, cDNAs can be prepared, for example, as follows: (1) synthesize cDNAs based on mRNAs extracted from rice varieties with the PSR1 gene (e.g. Koshihikari); (2) prepare a cDNA library by inserting the synthesized cDNAs into vectors, such as λZAP; (3) develop the cDNA library; and (4) conduct colony hybridization or plaque hybridization as described above. Alternatively, cDNAs can be also prepared by PCR.

The present invention includes DNAs encoding proteins (Kasalath) functionally equivalent to the PSR1 protein of SEQ ID NO: 3. Herein, the term "functionally equivalent to the PSR1 protein" indicates that modification of expression or activity of the object protein results in an increase in regeneration ability.

Examples of such DNAs include those encoding mutants, derivatives, alleles, variants, and homologues comprising the amino acid sequence of SEQ ID NO: 3 wherein one or more amino acids are substituted, deleted, added and/or inserted.

Examples of methods known to those skilled in the art for preparing a DNA encoding a protein comprising altered amino acids include site-directed mutagenesis (Kramer, W. and Fritz, H.-J., (1987) "Oligonucleotide-directed construction of mutagenesis via gapped duplex DNA." Methods in Enzymology, 154: 350-367). The amino acid sequence of a protein may also be mutated in nature due to the mutation of a nucleotide sequence. DNAs encoding proteins having the amino acid sequence of a natural PSR1 protein wherein one or more amino acids are substituted, deleted, and/or added are also included in the DNAs of the present invention, so long as they encode a protein functionally equivalent to the natural PSR1 protein (SEQ ID NO: 3). Additionally, nucleotide sequence mutants that do not give rise to changes in the amino acid sequence of the protein (degeneracy mutants) are also included in the DNAs of the present invention.

DNAs encoding proteins functionally equivalent to the PSR1 protein described in SEQ ID NO: 3 can be produced, for example, by methods well known to those skilled in the art, including methods using hybridization techniques (Southern, E. M., Journal of Molecular Biology, Vol. 98, 503, 1975.); and polymerase chain reaction (PCR) techniques (Saiki, R. K. et al. Science, vol. 230, 1350-1354, 1985; Saiki, R. K. et al. Science, vol. 239, 487-491, 1988). That is, it is routine for a person skilled in the art to isolate DNAs with high homology to the PSR1 gene from rice and other plants by using the nucleotide sequence of the PSR1 gene (SEQ ID NO: 2) or parts thereof as a probe, and oligonucleotides hybridizing specifically to the nucleotide sequence of the PSR1 gene (SEQ ID NO: 2) as a primer. Such DNAs encoding proteins functionally equivalent to the PSR1 protein, obtainable by hybridization techniques or PCR techniques, are included in the DNAs of this invention.

Hybridization reactions to isolate such DNAs are preferably conducted under stringent conditions. Stringent hybridization conditions of the present invention include conditions such as 6 M urea, 0.4% SDS, and 0.5×SSC; and those conditions which yield similar stringencies. DNAs with higher homology are expected when hybridization is performed under conditions with higher stringency, for example, 6 M urea, 0.4% SDS, and 0.1×SSC. Those DNAs isolated under such conditions are expected to encode a protein having a high level of amino acid homology with a PSR1 protein (SEQ ID NO: 3 or 6). Herein, high homology means identity of at least 50% or more through the entire amino acid sequence, more preferably 70% or more, and much more preferably 90% or more (e.g. 95%, 96%, 97%, 98%, 99% or more). The degree of homology of one amino acid sequence or nucleotide sequence to another can be determined by following the BLAST algorithm by Karlin and Altschul (Proc. Natl. Acad. Sci. USA 87:2264-2268, 1990; Proc. Natl. Acad. Sci. USA, 90: 5873, 1993). Programs such as BLASTN and BLASTX were developed based on the BLAST algorithm (Altschul S F, et al. J. Mol. Biol. 215: 403, 1990). To analyze a nucleotide sequences according to BLASTN, the parameters are set as score=100 and word length=12, for example. On the other hand, parameters used for the analysis of amino acid sequences by BLASTX include, for example, score=50 and word length=3. The default parameters for each program are used when using BLAST and Gapped BLAST program. Specific techniques for such analyses are known in the art.

Whether a particular DNA encodes a protein involved in the regeneration ability of a plant can be evaluated as follows. The most conventional methods involve deleting the function of a DNA, then cultivating, and investigating the ability to regenerate. More specifically, the methods involve cultivating under conditions where the function of a DNA is maintained, and under conditions where the function of a DNA is deleted, and comparing the resulting regeneration abilities. If the regeneration abilities do not change or are nearly the same, the DNA is not involved in regeneration ability. When the DNA is involved in regeneration ability, the regeneration ratio is further increased, and this difference is considered to be the degree of regeneration ability.

The DNAs of the present invention can be used, for example, to prepare recombinant proteins, and to produce plant transformants having altered regeneration abilities. A recombinant protein is usually prepared by inserting a DNA encoding a protein of the present invention into an appropriate expression vector, introducing the vector into an appropriate cell, culturing the transformed cells, allowing the cells to express the recombinant protein, and purifying the expressed protein. A recombinant protein can be expressed as a fusion protein with other proteins so as to be easily purified, for example, as a fusion protein with maltose binding protein in *Escherichia coli* (New England Biolabs, USA, vector pMAL series), as a fusion protein with glutathione-S-transferase (GST) (Amersham Pharmacia Biotech, vector pGEX series), or tagged with histidine (Novagen, pET series). The host cell is not limited so long as the cell is suitable for expressing the recombinant protein. It is possible to utilize yeasts or various animal, plant, or insect cells as well as the above described *E. coli*. A vector can be introduced into a host cell by a variety of methods known to one skilled in the art. For example, a transformation method using calcium ions can be used to introduce a vector into *E. coli* (Mandel, M. and Higa, A. (1970) Journal of Molecular Biology, 53, 158-162, Hanahan, D. (1983) Journal of Molecular Biology, 166, 557-580). A recombinant protein expressed in host cells can be purified and recovered from host cells or the culture supernatant thereof by known methods. When a recombinant protein is expressed as a fusion protein with maltose binding protein or other partners, the recombinant protein can be easily purified by affinity chromatography. A protein of the present invention can be prepared from transformed plants which have been generated by introducing a DNA of this invention into plants as described below. Thus, as described below, the transformed plants of the present invention include not only plants with a DNA of this invention introduced to alter their regeneration ability, but also plants with a DNA of this invention introduced to prepare a protein of this invention.

The resulting proteins can be used to prepare antibodies that bind to the proteins. For example, a polyclonal antibody can be prepared by immunizing immune animals, such as rabbits, with a purified protein of the present invention or a portion thereof, collecting blood after a certain period, and removing clots. A monoclonal antibody can be prepared by fusing myeloma cells with the antibody-forming cells of animals immunized with the above protein or its portion, isolating monoclonal cells that express a desired antibody (hybridomas), and recovering the antibodies from the cell. The obtained antibodies can be utilized to purify or detect a protein of the present invention. Accordingly, the present invention includes antibodies that bind to proteins of the invention.

The use of these antibodies enables one to distinguish the expression site of proteins involved in the regeneration ability of a plant body, or to determine whether a plant species expresses a protein involved in regeneration ability.

When producing a transformed plant in which regeneration ability has been increased by utilizing a DNA of this invention, a DNA encoding a protein of this invention is inserted into an appropriate vector, which is then introduced into a plant cell. The transformed plant cells obtained by these steps are then regenerated. Plant cells to which the vector is introduced are preferably plant cells with low expression of the DNA of the present invention. Herein, the term "plant cells" includes plant cells of various forms, such as suspension culture cells, protoplasts, leaf sections, and calli.

Vectors used for plant cell transformation are not particularly limited as long as they can express the inserted genes in the cells. Examples include the "pBI121", "pBI221", and "pBI101" plasmids (all from Clontech).

The vectors of this invention may comprise a promoter for constitutively or inductively expressing the proteins of this invention. Examples of promoters for constitutive expression include the 35S promoter of cauliflower mosaic virus (Odell et al. 1985 Nature 313:810), actin promoter of rice (Zhang et al. 1991 Plant Cell 3:1155), and ubiquitin promoter of corn (Cornejo et al. 1993 Plant Mol. Biol. 23:567).

Examples of promoters for inductive expression include promoters known to initiate expression due to extrinsic factors, such as infection and invasion of filamentous fungi, bacteria, and viruses, low temperature, high temperature, dryness, ultraviolet irradiation, and spraying of particular compounds. Examples of such promoters include the chitinase gene promoter of rice (Xu et al. 1996 Plant Mol. Biol. 30:387) and the tobacco PR protein gene promoter (Ohshima et al. 1990 Plant Cell 2:95), which are induced by infection and invasion of filamentous fungi, bacteria, and viruses, the "lip19" gene promoter of rice, which induced by low temperature (Aguan et al. 1993 Mol. Gen Genet. 240:1), the "hsp 80" gene and "hsp 72" gene promoters of rice, which are induced by high temperature (Van Breusegem et al. 1994 Planta 193:57), the "rab 16" gene promoter of *Arabidopsis thaliana*, which is induced by dryness (Nundy et al., 1990 Proc. Natl. Acad. Sci. USA 87:1406), chalcone synthase gene promoter of parsley, which is induced by ultraviolet irradiation (Schulze-Lefert et al. 1989 EMBO J. 8:651), and the alcohol dehydrogenase gene promoter of corn, which is induced by anaerobic conditions (Walker et al., 1987 Proc. Natl. Acad. Sci. USA 84:6624). In addition, the chitinase gene promoter of rice and PR protein gene promoter of tobacco can also be induced by specific compounds such as salicylic acid, and the "rab 16" can also be induced by spraying abscisic acid, a phytohormone.

In addition, the vectors may comprise a promoter of a DNA encoding a protein of the invention. A promoter region of a DNA encoding a protein of the invention can be obtained by, for example, screening a genomic library using a DNA comprising the nucleotide sequence of SEQ ID NO: 1 or 2, or a portion thereof, as a probe.

Furthermore, the present invention provides transformed cells to which a vector of this invention has been introduced. In addition to the above-mentioned cells used for producing recombinant proteins, the cells to which a vector of this invention is introduced include plant cells for preparing transformed plants. There are no particular limitations as to the type of plant cells, and examples are cells of *Arabidopsis thaliana*, rice, corn, potato, and tobacco. In addition to cultured cells, the plant cells of this invention include cells within plants, and also protoplasts, shoot primordia, multiple shoots, and hairy roots. Vectors can be introduced into plant cells by known methods, such as polyethylene glycol methods, electroporation, *Agrobacterium* mediated transfer, and particle bombardment. Plants can be regenerated from transformed plant cells by known methods, depending on the type of plant cell (Toki et al., (1995) Plant Physiol. 100:1503-1507). For example, transformation and regeneration methods for rice plants include: (1) introducing genes into protoplasts using polyethylene glycol, and regenerating the plant body (suitable for indica rice varieties) (Datta, S. K. (1995) in "Gene Transfer To Plants", Potrykus I and Spangenberg Eds., pp 66-74); (2) introducing genes into protoplasts using electric pulse, and regenerating the plant body (suitable for japonica rice varieties) (Toki et al. (1992) Plant Physiol. 100, 1503-1507); (3) introducing genes directly into cells by particle bombardment, and regenerating the plant body (Christou et al. (1991) Bio/Technology, 9: 957-962); and (4) introducing genes using *Agrobacterium*, and regenerating the plant body (Hiei et al. (1994) Plant J. 6: 271-282). These methods are already established in the art and are widely used in the technical field of the present invention. Such methods can be suitably used for the present invention.

Having obtained a transformed plant containing a DNA of the present invention in its genome, it is possible to obtain a progeny of the plant by sexual or asexual reproduction. It is also possible to obtain reproductive material (such as seeds, fruits, spikes, tubers, tuberous roots, stubs, calli, and protoplasts) from the plant or a progeny or clone thereof, to mass-produce the plant based on such material. Thus, the present invention includes plant cells to which the DNA of the present invention has been introduced, plants containing these cells, progenies and clones of these plants, as well as reproductive material of the plants and their progenies and clones.

Plants produced in this manner whose regeneration ability has been modified show changes in their regeneration ability and yield as compared to wild-type plants. For example, plants in which a DNA encoding PSR1 protein has been introduced under the control of rice actin promoter are expected to show an increase in their regeneration abilities. Use of the methods of this invention can increase the regeneration ability of rice, which is a useful agricultural crop. The present invention is further beneficial in the development of highly regenerative rice varieties.

Furthermore, the present invention provides polynucleotides comprising at least 15 continuous nucleotides, which are complementary to the nucleotide sequence of SEQ ID NO: 1 or 2, or their complementary sequences. Herein, the phrase "complementary sequence" refers to a sequence of one strand with respect to the sequence of the other strand of a double-stranded DNA comprising A:T and G:C base pairs. The term "complementary" is not limited to cases in which a sequence is completely complementary to a region of at least 15 continuous nucleotides, and includes cases in which nucleotide sequence identity is at least 70%, preferably at least 80%, more preferably 90%, and even more preferably 95% or more (for example, 96% or more, 97% or more, 98% or more, or 99% or more). Such DNAs are useful as probes for detecting or isolating the DNAs of this invention, and as primers for amplifying the DNAs.

The present invention also provides methods of genetic diagnosis for determining the presence of regeneration ability in plants. In the present invention, "determining the presence of regeneration ability in plants" is not only effective for determining the presence of regeneration ability in varieties that have been cultivated so far, but also includes determining the presence of regeneration ability in new varieties produced by crossing and genetic engineering techniques. These methods are particularly effective for determining the presence of regeneration ability in japonica rice varieties.

The methods of the present invention for evaluating the presence of regeneration ability in plants comprise detection of plant expression levels of DNAs encoding the PSR1 protein, and of the PSR1 protein. For example, if the level of expression of a DNA encoding PSR1, or of the PSR1 protein, is higher than in Koshihikari, the examined plant is determined to be a variety possessing regeneration ability.

The present invention provides methods for utilizing the PSR1 gene as a selection marker in the transformation of plants. Examples of previously used selection marker genes of transformed plant cells include the hygromycin phosphotransferase gene that gives resistance to the antibiotic hygromycin, neomycin phosphotransferase that gives resistance to kanamycin or gentamycin, acetyl transferase gene that gives resistance to the herbicide phosphinothricin, and bialaphos resistance gene that gives resistance to bialaphos. When using these genes, transformed plant cell cultures are obtained by culturing in a known selection medium containing a selection agent that is suited to the type of selection marker gene. When using the PSR1 gene as a selection marker, instead of these drug-resistance genes, if the plant cells to be transformed do not have regeneration ability, as in Koshihikari, transformants can be selected using the acquired regeneration ability as a marker trait, without the use of special agents and such for selection. That is, since non-transformants cannot regenerate, individuals that regenerated due to the effect of the PSR1 gene are assumed to be transformants. Furthermore, when utilizing the PSR1 gene as a selection marker for plant cells with regeneration ability, the transformed cells can be selected by adding a certain concentration of nitrite, which would inhibit the growth of non-transformants, to the selection media. The above-mentioned conventional drug resistance genes used to select transformants are derived from microorganisms; therefore, genetically modified agricultural products (GMOs) in which such genes remain have raised concerns regarding adverse effects on the ecosystem and on the human body. However, the methods for selecting transformants that use the PSR1 gene of this invention have advantages in that such concerns can be relieved and inexpensive genetically modified crops can be developed.

All prior art documents cited herein are incorporated by reference.

BEST MODE FOR CARRYING OUT THE INVENTION

Herein below, the present invention will be specifically described using examples, however, it is not to be construed as being limited thereto.

Example 1

Selection of Test Material and Production of Near-Isogenic Lines

Figure 1:
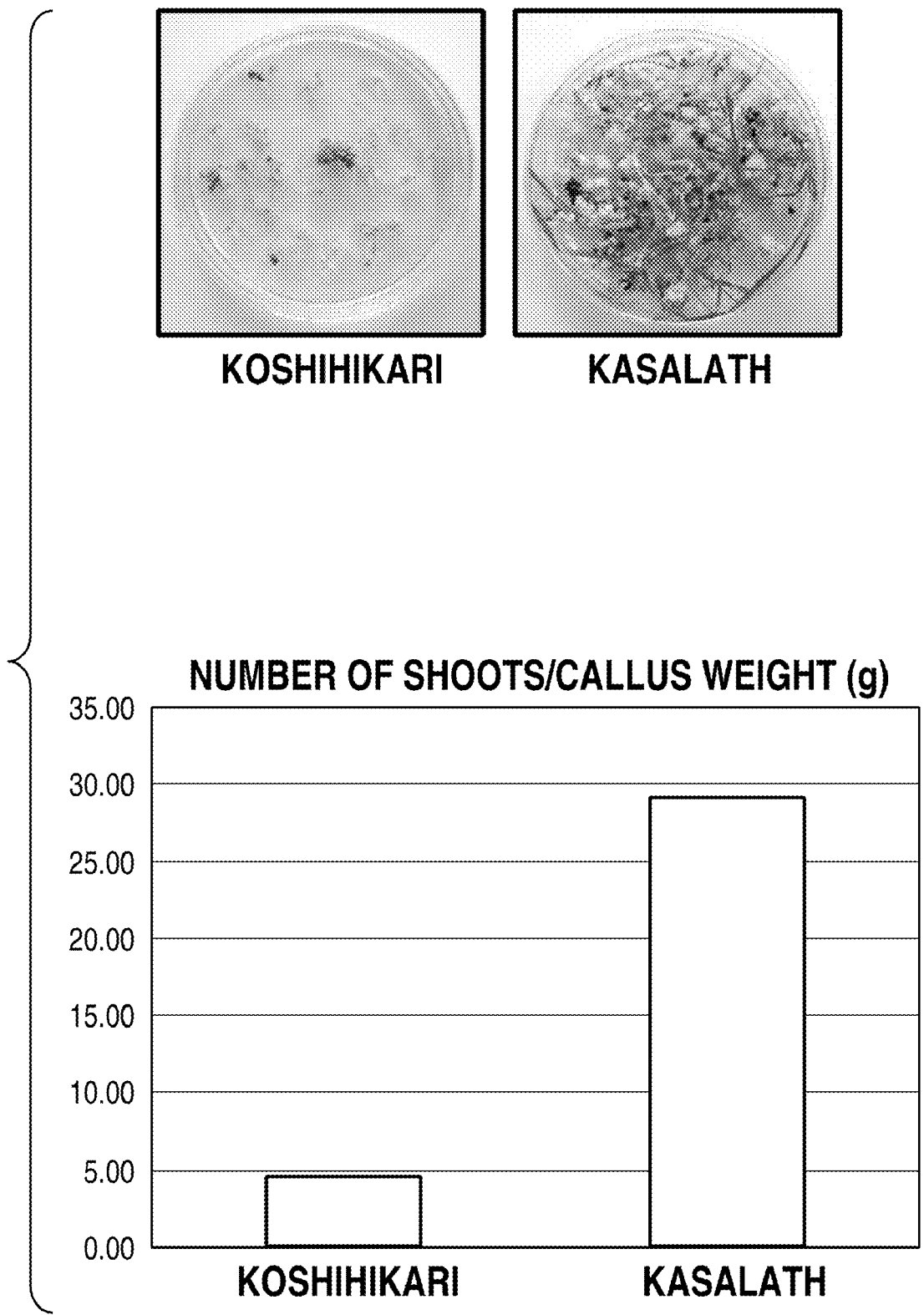
FIG. 1 is a graph and a set of photographs indicating the phenotypes of Koshihikari and Kasalath. The photograph on the left shows Koshihikari, and the photograph on the right shows Kasalath. The graph indicates the regeneration ability of Koshihikari and Kasalath as the number of regenerated individuals per gram of calli.

Prior to breeding a hybrid population for use in QTL analysis, varieties were selected to be the hybrid population parents. First, the average regeneration ability of several varieties of japonica rice and several varieties of indica rice were studied, and two varieties with a clear difference in regeneration abilities were selected: japonica rice "Koshihikari" and indica rice "Kasalath" (photograph FIG. 1). F1 individuals were produced by crossing japonica variety "Koshihikari" and indica variety "Kasalath". These individuals were then backcrossed using Koshihikari as the recurrent parent, and self-fertilized. After producing the BC1F1 population, BC1F2 seeds were collected. 20 BC1F2 seeds from each line were used to culture the calli in an induction medium for 30 days, then grown calli were transferred to a regeneration medium. 30 days after transfer, the callus weight and number of shoots per seed were measured, and average values were determined using the 20 seeds of each line. This was taken to be the regeneration ability (graph FIG. 1). Genotypes of each line were determined using 262 PCR markers.

Figure 2:
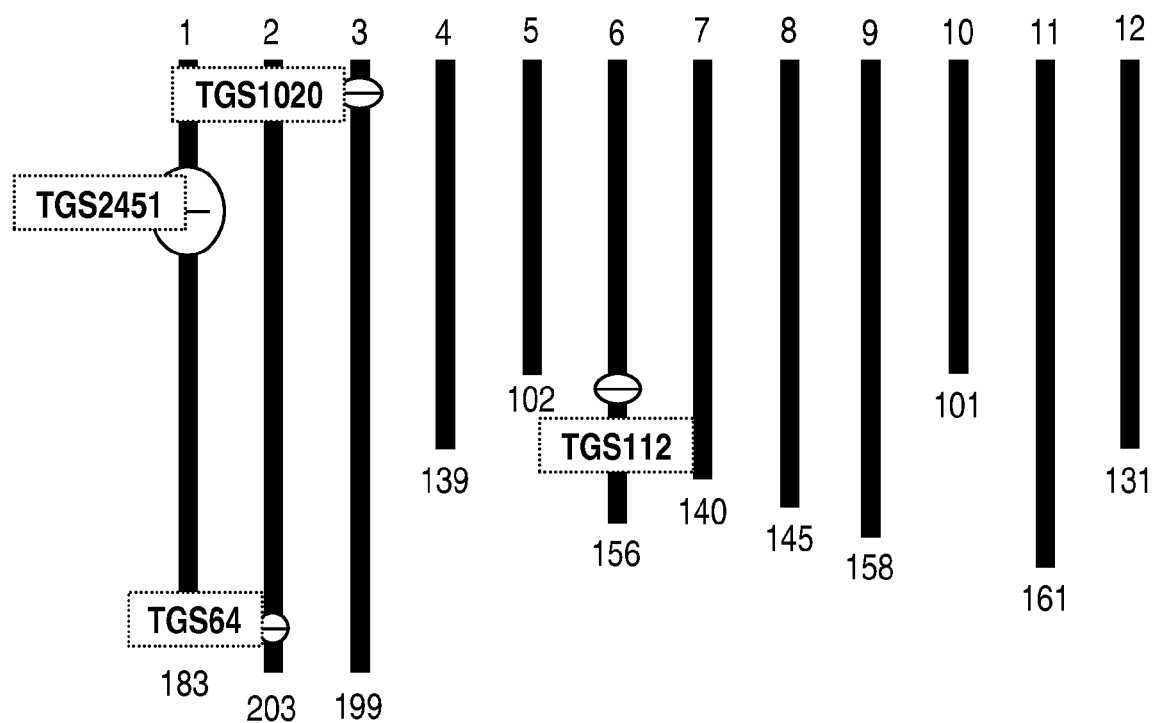
FIG. 2 shows the positions of regeneration ability QTLs on the chromosome.

When QTL analyses relating to regeneration ability were carried out based on these data, four QTLs having the effect of increasing regeneration ability were found (FIG. 2). It was successfully found that in one of these QTLs near the TGS2451 marker on the short arm of chromosome 1 (PSR1; Promoter of Shoot Regeneration 1), the Kasalath genome had a large increasing effect on the regeneration ability of Koshihikari. PSR1 near-isogenic line (Nil-PSR1: a line in which a substitution has been made on the Koshihikari chromosome using a region near the Kasalath chromosome 1 TGS2451 marker) was produced using repeated backcrossing and MAS. The regeneration ability of Nil-PSR1 and Koshihikari (control) was investigated, and the presence of QTL (PSR1) was confirmed. In the line in which the region near TGS2451 on the short arm of chromosome 1 had been substituted with that of Kasalath, regeneration ability increased an average of 14.7 times.

Example 2

High Resolution Linkage Analysis Using a Segregating Population of PSR1

Figure 3:
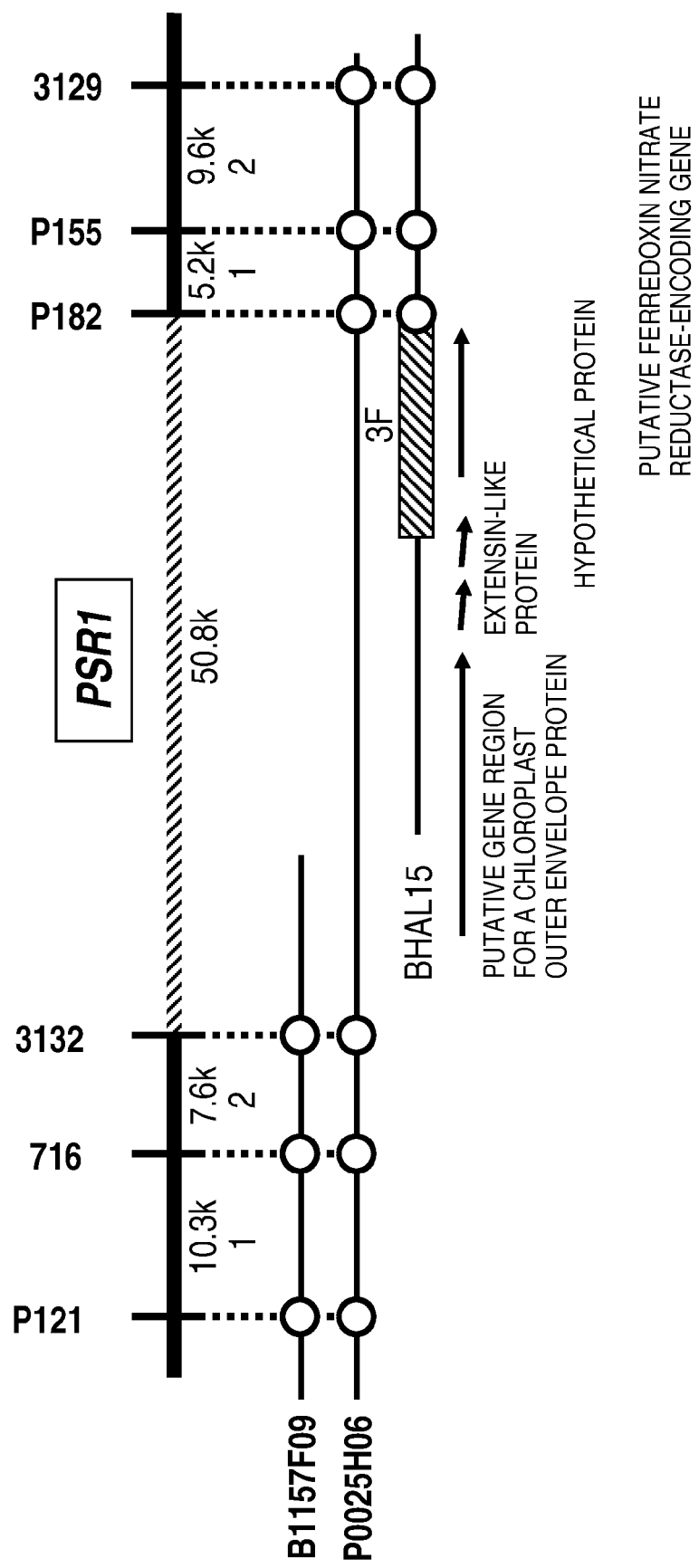
FIG. 3 shows a highly accurate linkage map of the regeneration ability QTLs.
Figure 4:
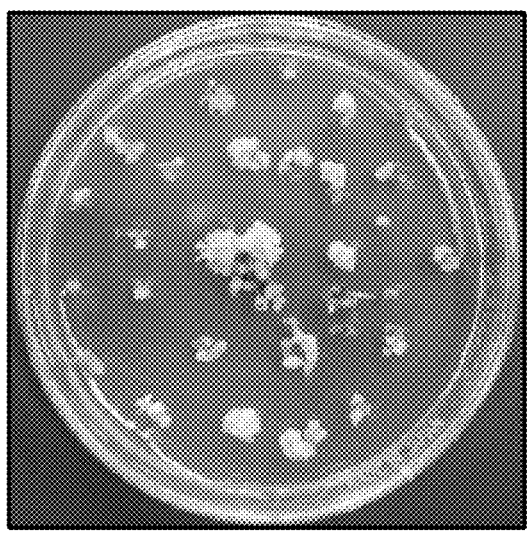
FIG. 4 is a set of photographs indicating the results of complementation tests. The left photograph shows the result when the vector alone is inserted into Koshihikari, while the right photograph shows the regeneration that occurs when the 3F fragment of Kasalath is inserted into Koshihikari.
Figure 4:
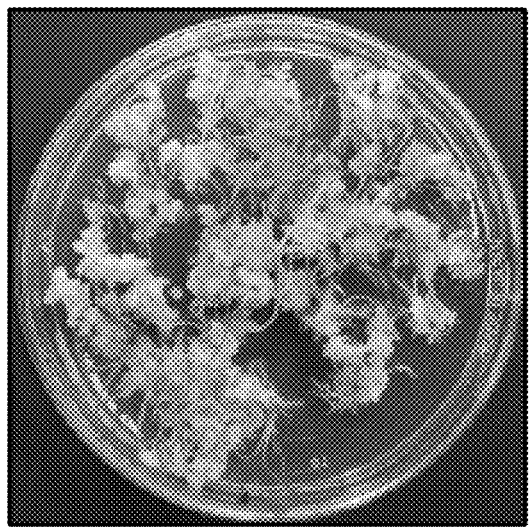
Figure 5:
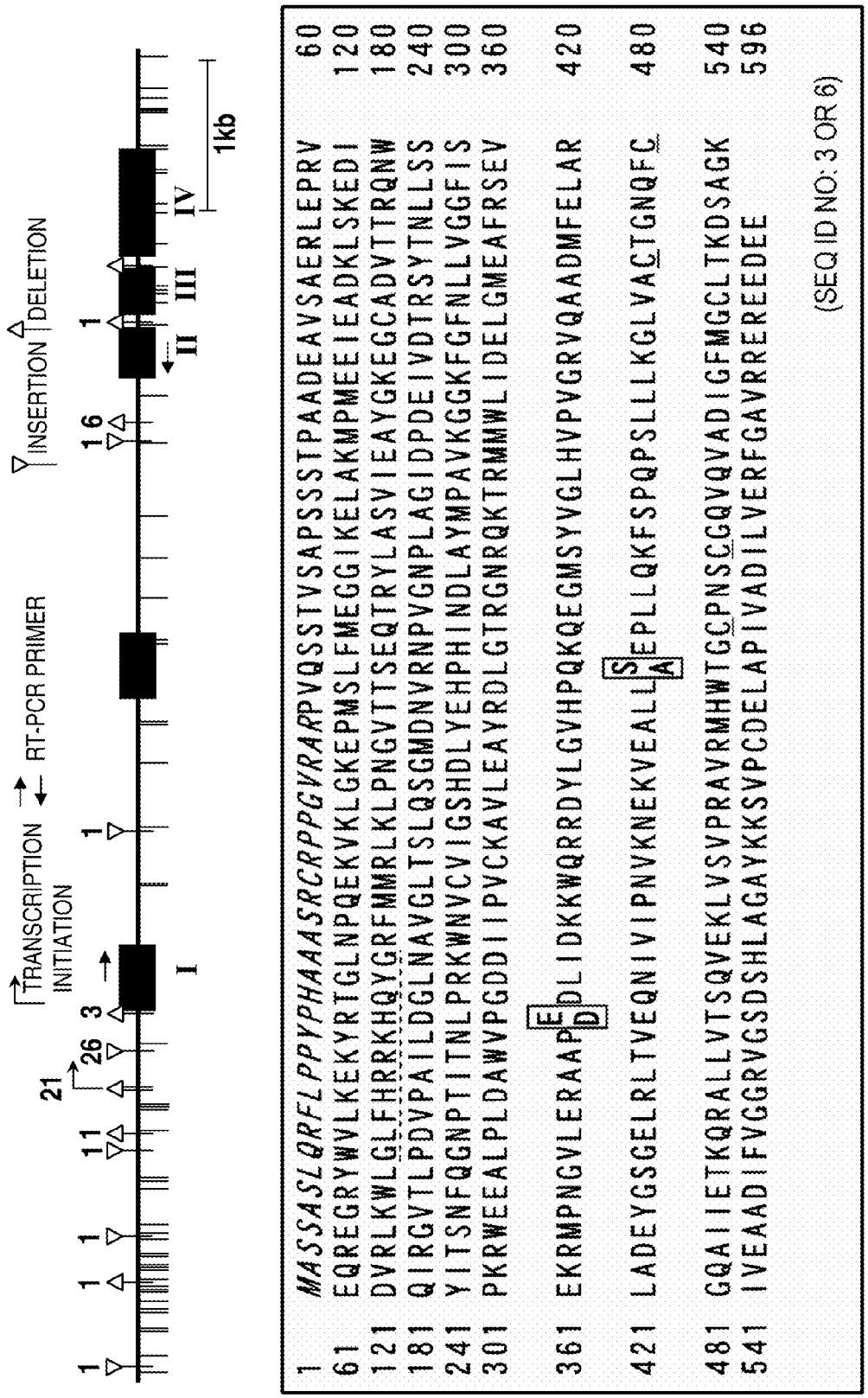
FIG. 5 shows the mutation sites of the Kasalath NiR genome compared to the Koshihikari NiR genome sequence. The Arabic numerals in the schematic diagram indicate the number of inserted or deleted nucleotides. Black squares indicate coding regions. Vertical lines indicate substitution sites. The framed part shows comparison of the NiR gene sequences in Koshihikari (top) and Kasalath (bottom). The parts enclosed in boxes indicate the amino acids that were different between Koshihikari and Kasalath. The region indicated in bold italics indicates the chloroplast transit peptide domain, the region indicated by the dotted underline indicates the ferredoxin binding region, and the underlined portion indicates the 4Fe-4S cluster.

30 individuals whose PSR1 region had been substituted with that of Kasalath were selected from the BC2F1 population. Ten of each seed (BC2F2 seeds) were used, and DNA was extracted from the calli. The genotype was elucidated using molecular markers, and linkage analyses were carried out by investigating regeneration ability. Furthermore, to specify the locus in detail, approximately 3,800 BC3F2 seeds in which PSR1 segregated were used to investigate genotype using molecular markers, and high resolution linkage analysis was performed. As a result, PSR1 was found to be located in an about 50.8 kb region between molecular markers 3132 and P182 (FIG. 3). Predictions of genes in this region suggested the presence of four genes, including a hypothetical protein. To determine which of these genes are regeneration ability genes, a Kasalath BAC library (average length 120 kb) was constructed, and a BAC clone comprising a PSR1 region (BHAL15) was isolated by PCR screening. Suitable restriction enzyme sites in the BHAL15 clone were used to prepare Kasalath genome fragments comprising each candidate gene region, and these were introduced to Koshihikari. As a result, it was found that the regeneration ability of Koshihikari increased only when the Kasalath genome fragment (3F in FIG. 3) comprising the gene expected to encode ferredoxin nitrite reductase (NiR) was introduced (FIG. 4). The nucleotide sequences of the genetic region predicted to encode ferredoxin nitrite reductase and the approximately 2 kb upstream thereof were determined and compared for Kasalath and Koshihikari, and many mutations were found in the nucleotide sequences (FIG. 5).

Example 3

Improving the Culturing Characteristics of Unculturable Varieties

Figure 8:
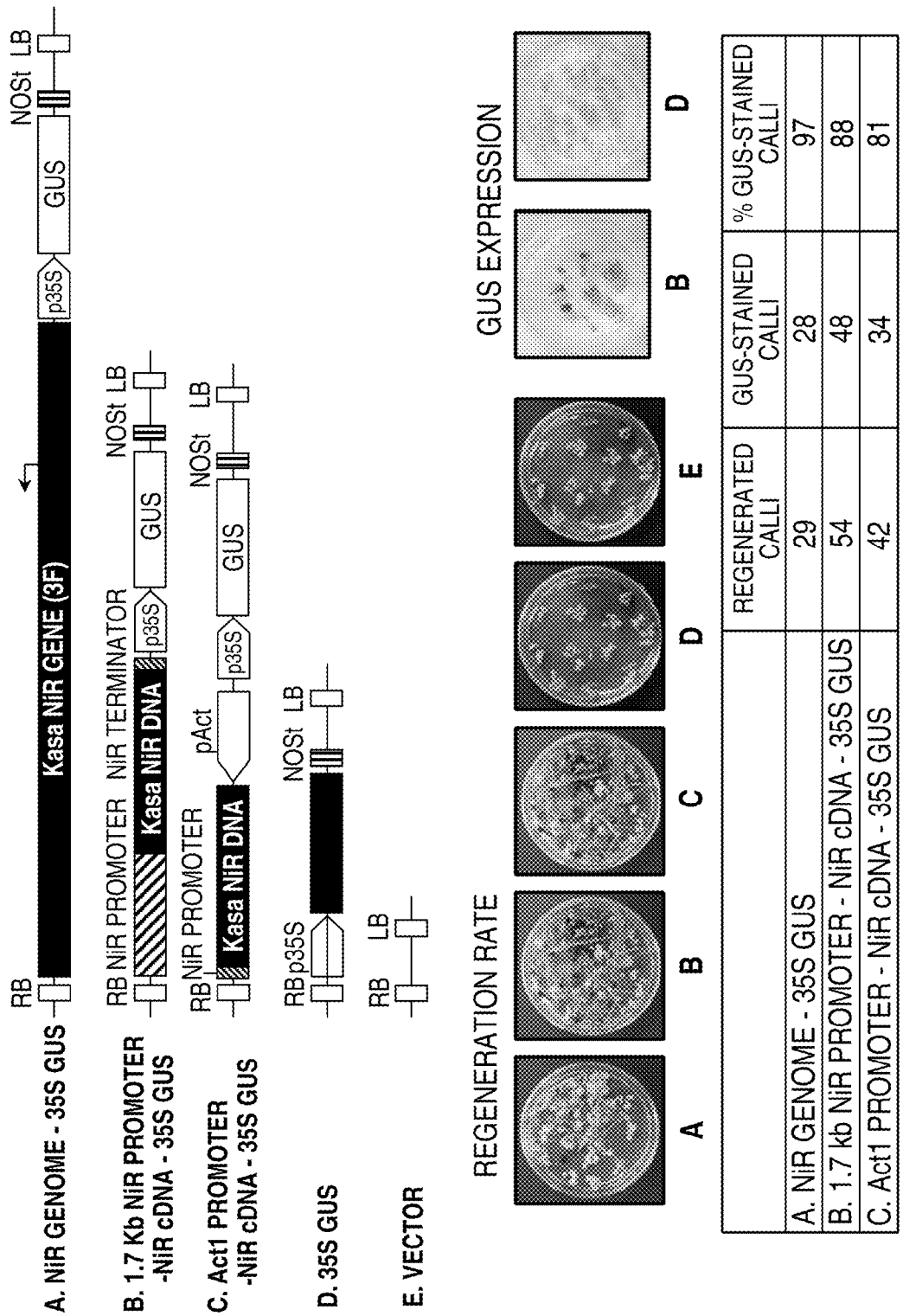
FIG. 8 is a diagram and a set of photographs showing the results of an experiment for confirming the effectiveness of the NiR gene as a selection marker. The schematic diagram shows the T-DNA region of the binary vector used for transformation. The photographs show the state of regeneration when each vector is introduced into Koshihikari. The table shows the proportion of GUS-stained individuals among the regenerated individuals.
Figure 9:
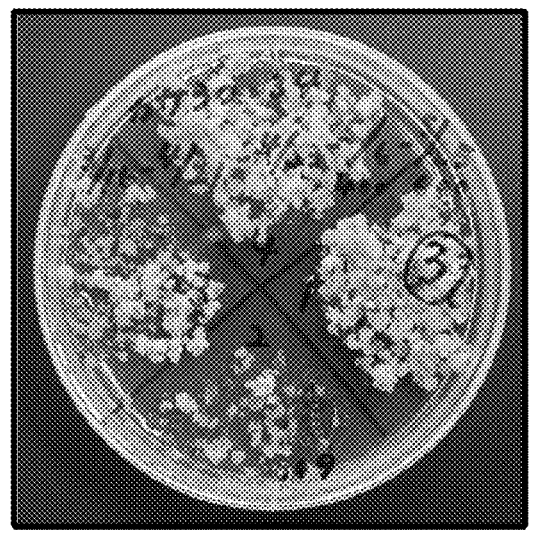
FIG. 9 is a photograph showing the result of selecting calli when a vector that overexpresses the NiR gene by the actin promoter is introduced into Kasalath. The top photograph shows the result of callus selection. Since nitrite was added to the medium, transformant "a" grew due to the effect of the overexpressed NiR gene, whereas callus growth of non-transformant "b" was inhibited. The bottom photographs show the GUS staining results for calli "a" and "b".
Figure 9:
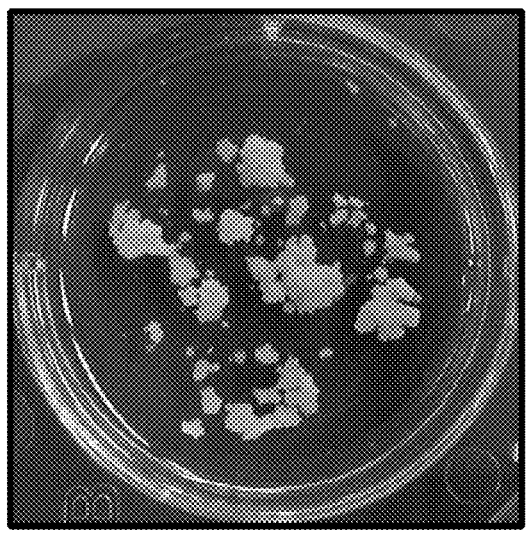
Figure 9:
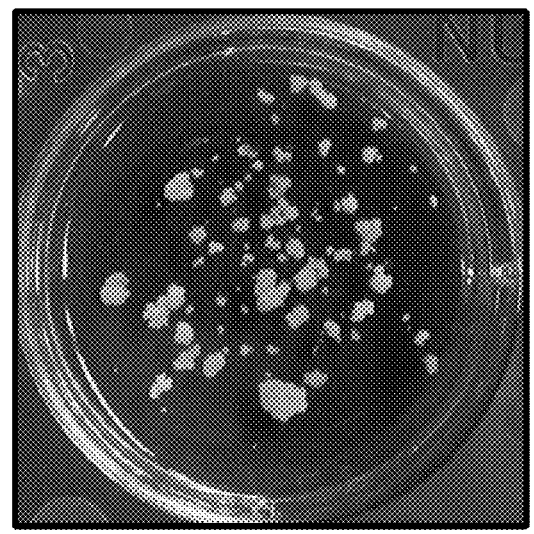

The PSR1 gene region of Kasalath (either the genomic sequence or cDNA sequence may be used) was introduced into Koshihikari to confer regeneration ability to Koshihikari, yielding highly regenerative Koshihikari (FIGS. 4, 8, and 9).

In this case, both PSR promoter and a constitutive promoter such as actin promoter were effective as a promoter used for expressing the PSR1 gene.

Example 4

Expression Analysis of the PSR1 Gene and PSR1 Protein

Figure 6:
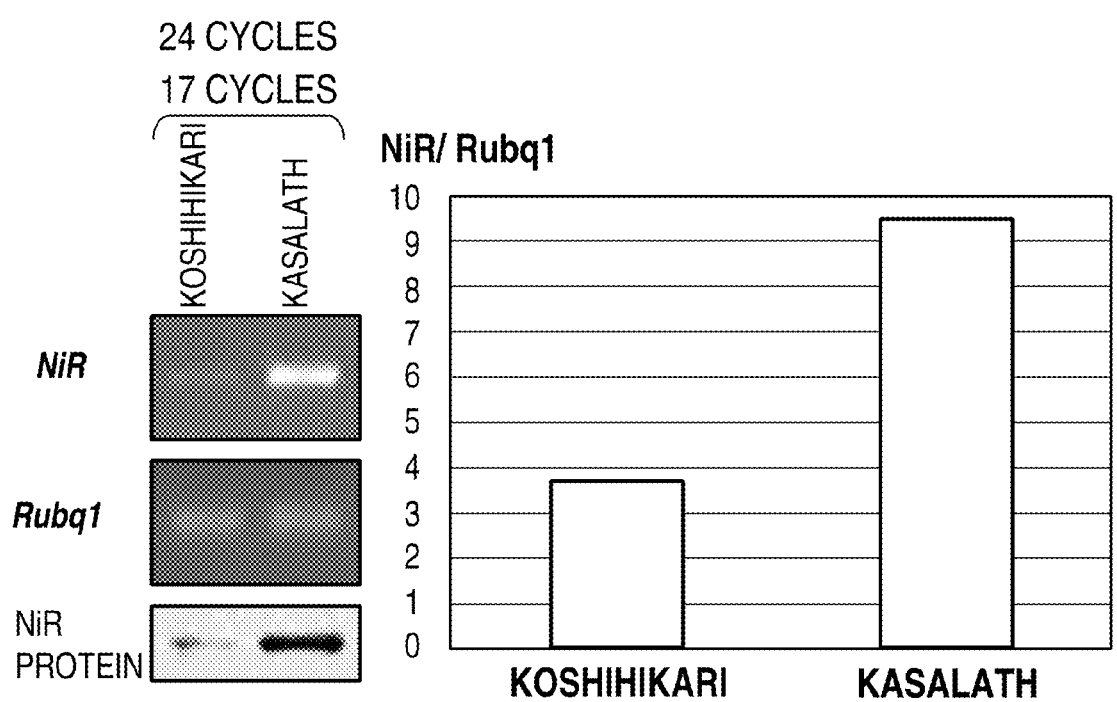
FIG. 6 is a set of photographs and a graph comparing the expression levels of the NiR genes and NiR proteins in the calli of Koshihikari and Kasalath. In the left photograph the top row shows the NiR gene as detected by semi-quantitative RT-PCR, the middle row shows the rice ubiquitin 1 gene (Rubq1), used as an expression control and detected by semi-quantitative RT-PCR, and the lower row shows the NiR protein as detected by Western blot hybridization using the NiR protein antibody. The graph on the right shows the results of measuring the expression level of the NiR genes by realtime quantitative RT-PCR using the expression level of the Rubq1 gene as an internal standard. The RT-PCR primer sites are shown in FIG. 5.
Figure 7:
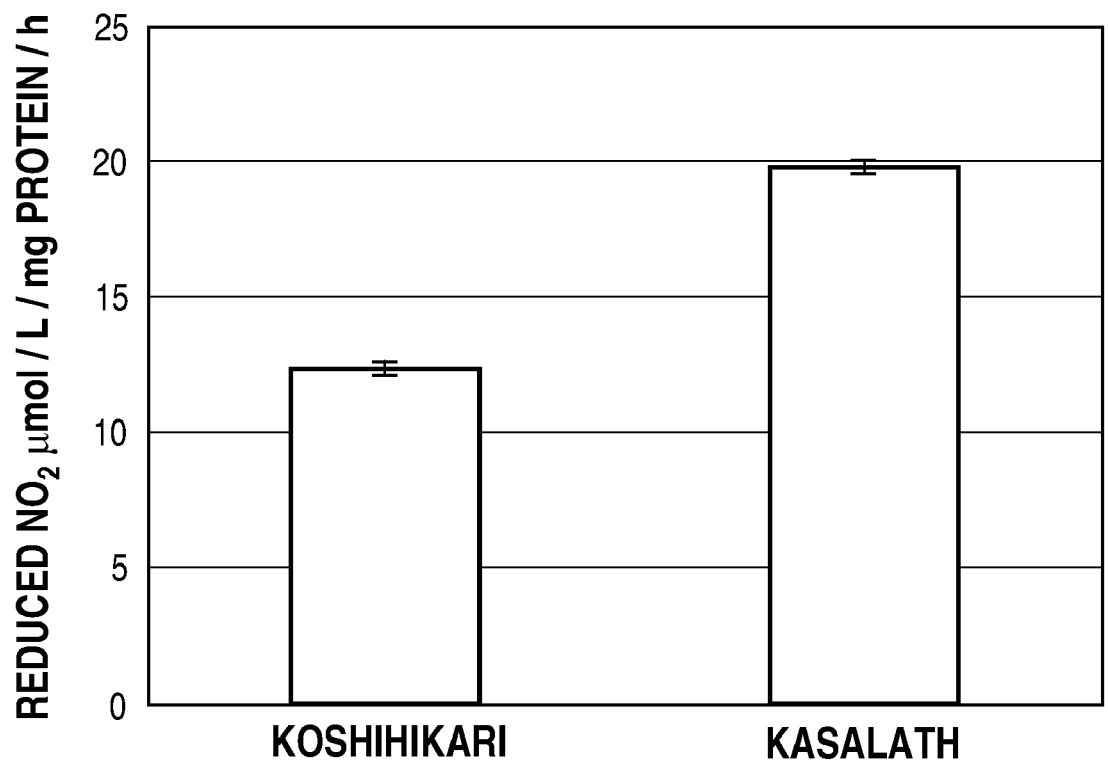
FIG. 7 is a graph comparing the enzyme activities of the Koshihikari and Kasalath NiR recombinant proteins.

When the expression levels of the NiR mRNA in calli were examined by semi-quantitative RT-PCR and real-time quantitative PCR, the amount of mRNA in Kasalath was approximately 2.5 times that in Koshihikari (top and middle rows of the photographs on the left, and the graph on the right in FIG. 6). Western blot analysis using antibodies specific to the NiR protein also showed that the NiR protein is stored in larger amounts in Kasalath than in Koshihikari (bottom row of the photographs on the left in FIG. 6). Furthermore, in a comparison of NiR enzyme activity per unit protein using the naphthyl ethylenediamine method and an NiR recombinant protein whose expression is induced by E. Coli, the Kasalath NiR protein showed enzyme activity approximately 1.6 times higher than that of Koshihikari (FIG. 7). The above-mentioned results showed that the difference in regeneration ability between Koshihikari and Kasalath is primarily due to the difference in the level of transcriptional regulation of the NiR gene, and is secondly due to differences in activity per molecule of the synthesized protein.

Example 5

Transformation that Uses Regeneration Ability as the Selection Trait

Introduction of the Kasalath PSR1 gene into Koshihikari can confer regeneration ability to Koshihikari, which does not regenerate. This indicates that Kasalath PSR1 gene can be used as a selection marker when transforming Koshihikari. More specifically, when a vector in which the Kasalath PSR1 gene and a target gene have been inserted tandemly is introduced into Koshihikari, only those cells to which the PSR1 gene has been introduced will acquire regeneration ability. Therefore, regenerated plant bodies should have incorporated the target gene at the same time. To prove this notion, vectors carrying the Kasalath NiR genome+35S promoter GUS, Kasalath NiR promoter::NiR cDNA::NiR terminator+35S promoter GUS, rice Actin1 promoter::NiR cDNA::NiR terminator+35S promoter GUS in the T-DNA region of the pBI101 binary vector, and a vector that does not carry the NiR gene were constructed, and introduced into Koshihikari. As a result, when three types of vectors comprising the NiR gene were introduced, many regenerated individuals were obtained, and staining due to the GUS gene was observed in the calli from which they were derived (FIG. 8).

In addition, the NiR gene has the property of metabolizing nitrite, which is toxic to plants, and utilizing this characteristic also allows the NiR gene to be used as a marker for transformation of highly regenerative varieties. More specifically, a vector that overexpresses the NiR gene under the control of an actin promoter, which is a high expression promoter in rice, was introduced into a highly regenerative Kasalath variety, and this was cultured on a medium supplemented with nitrite at a concentration that would inhibit the growth of ordinary wild types. Only transformed cells grew due to the effect of the overexpressed NiR gene, and GUS staining was observed only in these grown cells (FIG. 9). The use of this selection method enabled the cost of antibiotics to be reduced compared to conventional methods in which antibiotic resistance genes derived from microorganisms are used as selection markers. Additionally, this method enabled production of more environmentally-friendly recombinant plants since the regenerated plants do not contain microorganism genes.

INDUSTRIAL APPLICABILITY

Recently, studies utilizing transformation methods for the development of useful plants and for functional analyses of genes are progressing rapidly. Since transformation methods allow the use of genes beyond the confines of biological species, which is impossible in conventional breeding based on crossing and selection, novel plants may be produced. Furthermore, as genomic sequences are elucidated one after another, transformation methods are also being used for gene disruption, expression regulation analysis, and such to elucidate the function of each gene. Generally, when producing a plant transformant, a plasmid vector comprising both the gene to be introduced and a drug resistance marker gene such as an antibiotic resistance gene is introduced into plant cells by the Agrobacterium method or by electroporation, and transformed cells are selected by drug-treatment. The transformed cells that are selected regenerate into plant bodies through cell growth. Thus, to utilize such transformation methods, tissue culturing techniques must be established. Tissue culturing techniques are extremely useful not only in transformation methods, but also in mutant production using somaclonal variation, cultivar breeding using cell fusion or ovule culture, fixation of hereditary character, shortening of the number of years taken for breeding, and the like.

The major grain for which culturing techniques are most utilized is rice, but the presence of large differences in culturing characteristics between varieties is considered a problem. In particular, it is difficult to culture the major varieties in Japan, such as Koshihikari and Akitakomachi, as well as many indica varieties cultivated in the tropics, and therefore these varieties cannot be used as materials for tissue cultures. These differences in culturing characteristics between varieties are phenomena commonly observed in a number of plants and is not limited to rice, but there has been no progress in elucidating their causes.

The present inventors isolated genes involved in regeneration ability, enabling efficient selection of highly regenerative traits by using molecular markers (marker selected breeding), and enabling improvement of regeneration ability using molecular biological methods (molecular breeding). Furthermore, utilization of the PSR1 gene as a selection marker has enabled the production of inexpensive and environmentally considerate plant transformants.

Grains such as rice, corn, wheat, and barley are major energy sources for humans, and are the most important plants for humans. These grains all belong to the family Poaceae, and seem to have evolved from a common ancestor. They have high genetic homology (genomic synteny) with one another. Of these grains, rice has the smallest genome, and this is why rice is used as a model plant for grains. Rice genes are present in the genomes of rice relatives such as wheat and corn, and genes isolated from rice can be easily isolated from wheat and corn. In addition, rice genes can be applied directly to grain breeding of wheat, corn, and such. Therefore, the present genes may be applied not only to rice but also to wide varieties of plants.

The invention claimed is:

1. An isolated DNA selected from the group consisting of:
   (a) a DNA encoding a protein comprising the amino acid sequence of SEQ ID NO: 3; and
   (b) a DNA comprising the coding region of the nucleotide sequence of SEQ ID NO: 1 or 2.

2. An isolated DNA comprising a promoter region and the coding region of the nucleotide sequence of SEQ ID NO: 1 or 2.

3. A vector comprising the DNA of claim 1.
4. A vector comprising the DNA of claim 2.
5. A host cell carrying the vector of claim 3.
6. A plant cell carrying the vector of claim 3.
7. A plant transformant comprising the plant cell of claim 6.
8. A plant transformant that is a progeny or a clone of the plant transformant of claim 7.
9. A propagation material of the plant transformant of claim 7 or 8, wherein the propagation material retains a DNA encoding a protein comprising the amino acid sequence of SEQ ID NO:3 in the expressible manner.
10. A method for producing a plant transformant, wherein the method comprises the steps of introducing the DNA of claim 1 into a plant cell, and regenerating a plant from said plant cell.
11. A method for producing a protein comprising the amino acid sequence of SEQ ID NO:3, wherein the method comprises the steps of culturing the host cell of claim 5, and collecting the recombinant protein from said cell or the culture supernatant thereof.

12. A method for increasing the regeneration ability of a plant, wherein the method comprises the step of expressing the DNA of claim 1 in a cell of a plant.

13. An agent for increasing the regeneration ability of a plant, wherein the agent comprises a DNA encoding a protein comprising the amino acid sequence of SEQ ID NO:3, or the vector of claim 3 as an active ingredient.

14. A method for determining the regeneration ability of a plant cell, wherein the method comprises the step of detecting the expression of a DNA of claim 1 or a protein encoded by the DNA of claim 1 in the plant cell.

15. A method for determining the regeneration ability of a plant cell, wherein the method comprises the step of detecting the activity of a protein encoded by the DNA of claim 1 in the plant cell.

16. A method for improving the regeneration ability of a plant, wherein the method comprises the step of increasing the activity of an endogenous protein encoded by the DNA of claim 1 in the plant.

17. A method for selecting a transformed plant cell, wherein the method comprises the steps of:
  (a) introducing a plant cell with a vector comprising the DNA of claim 1 as a selection marker; and
  (b) culturing the plant cell and selecting plant cells that have acquired or increased regeneration ability when compared to an untransformed plant cell.

18. A method for increasing the regeneration ability of a plant, wherein the method comprises the step of introducing the DNA of claim 1 in a plant by crossing.

\* \* \* \* \*

UNITED STATES PATENT AND TRADEMARK OFFICE
CERTIFICATE OF CORRECTION

| | | |
|---|---|---|
| PATENT NO. | : 7,790,957 B2 | Page 1 of 1 |
| APPLICATION NO. | : 10/566593 | |
| DATED | : September 7, 2010 | |
| INVENTOR(S) | : Nishimura et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 866 days.

Signed and Sealed this
Third Day of May, 2011

David J. Kappos
*Director of the United States Patent and Trademark Office*

SEQUENCE LISTING

<160> NUMBER OF SEQ ID NOS: 6

<210> SEQ ID NO 1
<211> LENGTH: 12161
<212> TYPE: DNA
<213> ORGANISM: Oryza sativa
<220> FEATURE:
<221> NAME/KEY: exon
<222> LOCATION: (6010)..(6418)
<223> OTHER INFORMATION:
<220> FEATURE:
<221> NAME/KEY: exon
<222> LOCATION: (10247)..(10601)
<223> OTHER INFORMATION:
<220> FEATURE:
<221> NAME/KEY: exon
<222> LOCATION: (10703)..(10991)
<223> OTHER INFORMATION:
<220> FEATURE:
<221> NAME/KEY: exon
<222> LOCATION: (11076)..(11813)
<223> OTHER INFORMATION:
<220> FEATURE:
<221> NAME/KEY: misc_feature
<222> LOCATION: (4429)..(4429)
<223> OTHER INFORMATION: "n"=a, t, g or c.
<220> FEATURE:
<221> NAME/KEY: misc_feature
<222> LOCATION: (4479)..(4479)
<223> OTHER INFORMATION: "n"=a, t, g or c.
<220> FEATURE:
<221> NAME/KEY: misc_feature
<222> LOCATION: (4520)..(4520)
<223> OTHER INFORMATION: "n"=a, t, g or c.
<220> FEATURE:
<221> NAME/KEY: misc_feature
<222> LOCATION: (4555)..(4555)
<223> OTHER INFORMATION: "n"=a, t, g or c.
<220> FEATURE:
<221> NAME/KEY: misc_feature
<222> LOCATION: (4561)..(4561)
<223> OTHER INFORMATION: "n"=a, t, g or c.
<220> FEATURE:
<221> NAME/KEY: misc_feature
<222> LOCATION: (4563)..(4563)
<223> OTHER INFORMATION: "n"=a, t, g or c.
<220> FEATURE:
<221> NAME/KEY: misc_feature
<222> LOCATION: (4577)..(4578)
<223> OTHER INFORMATION: "n"=a, t, g or c.
<220> FEATURE:
<221> NAME/KEY: misc_feature
<222> LOCATION: (4823)..(4823)
<223> OTHER INFORMATION: "n"=a, t, g or c.
<220> FEATURE:
<221> NAME/KEY: misc_feature
<222> LOCATION: (7186)..(7186)
<223> OTHER INFORMATION: "n"=a, t, g or c.
<220> FEATURE:
<221> NAME/KEY: misc_feature
<222> LOCATION: (11994)..(11994)
<223> OTHER INFORMATION: "n"=a, t, g or c.

<400> SEQUENCE: 1

```
ctcgagcttt tttgactgcc ctaatcaggc gggttccttg tgggacccac ataatgcttt      60
ttttaatcgc cttcacgggc tgcatgcaaa ctatacggca tgggacttcc actactagaa     120
aaaacgggcg gtcgaaacac gttttcgcag gcaggcaaac cttccacatg tatcttaacg     180
accgtaaaaa tctccaattt tcacaggtgg accacagcac cgttttcgca ggctacattt     240
cgaatcttcc tgggtgctac agtaaaccac ctgcaaaaat actcacggcg ccaaaaaaaa     300
tttccgccag ccccgccccc tccctattca aatcacaaat cacaaattct cacaaatctc     360
```

-continued

```
atccaaaaac aaaatccaat ccaaaaatcc atacatcaac acaaagcatt ggattcaaat    420
ccacaacatc aatttacaag ttaacatcaa tcaacatgta agctttaaaa cgaaacgtcg    480
tcgtcgccgg caaactcctt tgcatgcggt gccgctgccg ccccctccc cctctgtccg     540 gatttgggag ggagggaggg aggtgtttgc cgccaccacc gccctcccct ctcctcgtag    600
ggccggatct cggagggag gagagggag ccgcctccgc acagccatca acgtccgtgc      660
cgccgtcgcc tcgttcgcac caccgccgtt gcttcccctc ctccggccag atctaggagc    720
ggggaggaag agaggggag ccaccgccac cgtcgccccc tcgcgtccgc gccgtcgtca     780
ccgtccacgc cgccgcgtcc gtgccgccgc tgtcgctccc cctcctctgg cgaggaggga    840
gagagaggga gccgtcgcgc cgccgtcgct cccctccttc ggcgaggagg gagagagggg    900
gagggaagag ggatggaggg gaggagagtg gcgctgagag agagagagag agacgctgag    960
gagaggaaat gagtggtggg gagggtgga ggagaagata aggaggactt agattttttt    1020
ttgggtaggt atgattttg caggcggacc acataaggtt ccgcctgcga aaatcaattt    1080
tttcacgcag accacttaag aggtccgcat gcgaaaataa aggtattttt ttaggcagac    1140
ctcttaagtg gtccgcctgg aaaaattgat tttcacaagc agatgacgaa aattcacccc    1200
ggtttatatt ttcgaagatg cttcatcgac gacatcgacc gcgtcctcta tgacggcaac    1260
gaccgcgtca ccgacaacgg catcgatcac gtcatctacg atgacaacga ctgcatcaac    1320
tccgcatcac tattgtgatg actgttacat ggcgtagaag aaccaaccaa agtggtggcc    1380
tcatcgccaa cgacgtcctc tgacatatgc aagacgtccc caatggcatc ctcagacatc    1440
tacaaggtgc aagatgctaa caattacagt ttttgtcttc acactgtggc ataaatattt    1500
tttttcgcct tcggctatat tcggctacac ctacaaccac ggttactaca tgatcggctc    1560
catcaacgaa catctataac aacaatcatt gacggaaact ccagtcaaga gcgtctgtgt    1620
catcgctatc ttccatgaca ctcccgctat gactacgtga gggaatagag gagagtcaag    1680
ggacgacacg gaaggagacg taggcaccag gtggaggacc gtccatcaaa gatgcaattg    1740
atgatggtga gttgaagaag atgaagaaat aaaagatttc aaatccagtc gcaatcgttc    1800
gcttcgctcc cgttacgact gaggggggaat gttagaagca tagatatatt aattggagat    1860
aagagtcata caaatataga gataagatat catcctagag atagaattct atagataaaa    1920
tagagtccta gagataaatc tactcttact tgtaccccta tatataccc atgagaggat     1980 caatgcaata caccgagaat acaacaatta gattttttta cagttgtaac tatgatacgt    2040
tgtaatatgc tggatcgggg aagagcgccc gtaatcagtg ccccagagat gtaggtctcg    2100
gctgaactcc attatcaaat accgtacctc ggtgttgtca tcatgtttga atcttctatg    2160
acgtttcttt tgcattcggt tttcgatgtg acttcagggc tggttttata ataatgatta    2220
tagtgctgtg acggcaatcg gttgtgagaa ttagctattc gggtccctcc atgtgatttt    2280
cttgtgattg ggatgtatgg taatgctagg gttttaaggt gtaggattgg tgcatgagag    2340
atcatcactt cacttgtatg accttctctc cttttatatt ttttttatcat tctctccttt    2400 tttttataat gctactgaac tagtggaata caggggacta atgcaaaata aagaaaagt    2460 atcactggtc acggcataca atttagaaag tgtgtgattt aggcatagag ctgaccacga    2520 cccctttacga cttggtcgct cggtttgtta gacgatagat caaccaacaa aagctacgat    2580
acatgatgta cgtgtcagga tacaaatcct tacaaataac aacagttatt gttcgataac    2640
ttttatcagt tgtctaggct taccaatgta taatagaaga tgaaaattcc atattactgg    2700
```

-continued

```
tatcgatcaa tgctagtaac tctttgagct ttgtctaggt taaaaaaaat tatggatcca    2760
ccatcacaaa aatgaaaaac accggggaaa acaaaaaacc atttaataac agcacaagac    2820
aaaatgatgt taccgtctac ccgagctcct actccgtacc agcacaacca aacgaacagt    2880
acccgccggg tcagggcac  gttcgtaaat ttccctcccg tggctggctg gctgccatct    2940
ctctcagcca gggttggtaa tttcggccgt ttcggtgggt cccgatagta aatgagctcc    3000
agtcaaaacg ccctctgcct cccctcattg cgccacacgc acaccgcatc tagatccaga    3060
tcgaaaaaat cgccatctcg ccgagtcgcc agtcgccgcc tcaacgccgg tcgccgtacc    3120
gccggcgctg cacgccccc  tccaagccgt cgccccatcg ccccagccg  ccggtggtg     3180 gggcagcgga tgccgagctt ggcgaggttg ccgaggacga accaggcgag gaggacgagg    3240
atcttgtcga cgagccagag cgggagccac gccatgagca acacggcgag ctcgaacgtg    3300
gacttgccga gcacctcgcc agggaggacg tggacggcgt cgcgcaccac catcgccggg    3360
agggcgctgt ggtcgcagag gtcgagcgac accaccatgc cggagttgcc gcacccgacg    3420
acgagcacct tcttgccgcg gtacgcctcg ccggacttgt agaccgcgac atgcatcacc    3480
tcgctgctat atttgttctt ggactgtgga gacttgctgt cagtgggtgt gttcagaatt    3540
gctgctgcag cttgcagcga atttgtgatg cagcagctac agcttgtatg gctgccgagt    3600
agagcgagtg ttgctatctg tttttttgttc tcttttttcag aaatttcgcc cgcaaatttt   3660
aaatttgaat tcaaattttt aaaagaacta gcaaatatgc ccgtgcgttg caccgggtga    3720
atatcaaaca aatattgatg ggtaagattg cttgtgtact tataacacat atgcacaaaa    3780
atattgaata tgtacatacc tcgcaaatat ctccaaattt tatacatatg agttgtgtaa    3840
atcgtgtgag ttccatattg tcatgttgat atggagtatt actgatgagc ccatctatgg    3900
tgataatttt ggaggttgta gctcaacgaa tttgtatttg ctatgtatct caacgttgat    3960
aagtcactac cacaaccatc ggcgaccttt tcgggatccc aagcatgttg accccgccaa    4020
cgtggcgtcg gtgcagggca ccgagatgaa caccacgggg ctatgtgcct gtccagggtc    4080
atcctaggct taaggccacg acactcaagg acgtggtggg cggcgtcgcg gaggtgctcc    4140
aagcgaacaa gctggccacc aaggaggacg ccgacaaggt ggcggccacc gctatgcaga    4200
acgatgggag gcacgccggt gacgacaagg agctaacacg atccatttag tcccgatccg    4260
agttgatcag gaattcaatc ctgcaccttg cggttacgtt tttcttctcc gcgggaaaag    4320
caatcaccga tggtagggac aaagtgtgtg tgagaacgga ggccaggcca aagtgcgtgc    4380
gagaacggag gctaggccat cgctggattg gatttacgaa tgaaatatng atgtgacgaa    4440
cagaaaatta tcagtttgat ttaattttca taatcggang tctttaatag gaaaaaaaat    4500
tacatgtacg ttccttcatn gtgcccatgt ccatccggga gtccaggttt attcncaaag    4560
ncncaatcaa cagctannaa tccatgtcct tccccgccgt tccctactct gcttttttt     4620 cttcatttg aaaccttccg ctatgaattt ctagtcgttc ctagcatcca cgcacacaaa     4680
atagatttcc ctcgcaaggc aaaacataca aatatgagtg catgcaagat attacaaacc    4740
caatccatta aaaatagaac ataattaact ttagcctacc tatctcaata ttggtatatg    4800
cccaaactca aaaggagaaa aancaaacta aaactttaa  taaagtgacc caagagata     4860 aaaaggtgat agtaacaaca aaatctcact tgacaatgtc gttgatcagc actattttta    4920
aatattactt aaaaatcttt atatttacct attaaaacaa tgaaaaacag aagatgtttc    4980 tttttttattt acaacagcgt tgtatttagt catgtcctat ctaagagaga aaaatgaatt   5040
taacgaaaag aagctcagaa aaaaaaaga  gaacagggcc accacaccag taatccctat    5100
```

```
gttatcaatg aaaaaaaatt tcaatgctag gttttttata agaaaaggtg ataaagtgtt      5160
gaaaaataca gcaggaaatt atatatcttg ctggtttaac attaattcaa gcatatagat      5220
ataaaaatat atcaggctag gaaaggaaaa ggataaaatt ggagagaaaa aggaaaagaa      5280
cagtagagga taaccagcaa aaagatgaaa ggattcgaac ccatgaccta gcgttacaat      5340
tgtttcacag gctaaccaat cgagaatcat cgacgtagtg taatcttgtg tagctacatt      5400
tgaaaaaata tgttttgagc tgaacgttgg tgtgtccgcc cctgcatccg atacatgttg      5460
gagcgtggag cgcggtaata tctccttctc tctcgtcgct ttctgcgtct ccccgtctct      5520
ccttcgccaa cagccgagaa gaggcagaga gagcgccgcc ccccgtccct ctctctccct      5580
ctcgtcctcg cccccatccc tctcgtctttt cccttgccgg cagcagagga ggcggcagcg      5640
acggcttcag ctgctcccac gggccggatc gggcagtggc ggtggcgtcg gcggcttccg      5700
ctggcgaatc cggcgggtga atcgggtgaa atttgggtga ccccccgatac aaatcagtgt      5760 tccgataggt aataccctgc tctcagcatc tgccctttttg aattcgccaa gagccagcat      5820
ctgccctttt gaattcgcca agggccagca tctgcccatt tgattttgaa ttcgccaaga      5880
gccagcaaca gcgccccgc gcccccctccc tcctccgcaa taaacagcca cacgcgccgc      5940
ccccatgtcc accctcatcg ccacagcgca ccaccaccac caccaccacc accaccaccg      6000 tctccagcc atg gcc tcc tcc gcc tcc ctg cag cgc ttc ctc ccc ccg tac    6051
           Met Ala Ser Ser Ala Ser Leu Gln Arg Phe Leu Pro Pro Tyr
            1               5                  10 ccc cac gcg gca gca tcc cgc tgc cgc cct ccc ggc gtc cgc gcc cgc        6099
Pro His Ala Ala Ala Ser Arg Cys Arg Pro Pro Gly Val Arg Ala Arg
 15                  20                  25                  30 ccc gtg cag tcg tcg acg gtg tcc gca ccg tcc tcc tcg act ccg gcg        6147
Pro Val Gln Ser Ser Thr Val Ser Ala Pro Ser Ser Ser Thr Pro Ala
                 35                  40                  45 gcg gac gag gcc gtg tcg gcg gag cgg ctg gag ccg cgg gtg gag cag        6195
Ala Asp Glu Ala Val Ser Ala Glu Arg Leu Glu Pro Arg Val Glu Gln
             50                  55                  60 cgg gag ggc cgg tac tgg gtg ctc aag gag aag tac cgg acg ggg ctg        6243
Arg Glu Gly Arg Tyr Trp Val Leu Lys Glu Lys Tyr Arg Thr Gly Leu
 65                  70                  75 aac ccg cag gag aag gtg aag ctg ggg aag gag ccc atg tca ttg ttc        6291
Asn Pro Gln Glu Lys Val Lys Leu Gly Lys Glu Pro Met Ser Leu Phe
         80                  85                  90 atg gag ggc ggc atc aag gag ctc gcc aag atg ccc atg gag gag atc        6339
Met Glu Gly Gly Ile Lys Glu Leu Ala Lys Met Pro Met Glu Glu Ile
 95                 100                 105                 110 gag gcc gac aag ctc tcc aag gag gac atc gac gtg cgg ctc aag tgg        6387
Glu Ala Asp Lys Leu Ser Lys Glu Asp Ile Asp Val Arg Leu Lys Trp
                115                 120                 125 ctc ggc ctc ttc cac cgc cgc aag cat cag t gtatgcctct cttctcttgc        6438
Leu Gly Leu Phe His Arg Arg Lys His Gln
                130                 135 tcctctgatc aacacatttt cttgctttcg ttcggttatt tgtcgcgccg aggaagttaa      6498
ttcgccaaga tattctgcag ttttttttct cgatgcacat tcagcaacct aattaagact      6558
gattaagttg ctgtgatttt tatagcttaa ttacggtctc gtgggtaatg actatttata      6618
ttgagtaaac atggttacct ttgatccaat cacttcacct ccatgtgcca tatatagcca      6678
caggctctac caagtaacac tagtaatatg cccgtgctac gacacggtgg cataataaat      6738
cattaaattt tattataatc aaattaagga tcctaaaatt ggtccaattg ggtgttaatt      6798
```

```
cgatgcaggt catataaaaa tatattttag gcaaggtgca attcaagagc atcaaccatt    6858
atatccaatc actttaatat atatttgaag ataacatatg tcggaaaaaa aatgatggag    6918
agctatttca ttaacttgtg agcataaaca gatcaccaga tgatgccacc ataagtcccg    6978
ccacagtaag tgatgcagct catcttgccc taggcgttcg gtctaaccag tagatagaaa    7038
gagtacaaca tagatcgaat gaaaaaaaaa atctccagaa gaaagctcaa ccacattgag    7098
taaattagag caacaatcaa atcgagtcag catatcgtta tgttagcaga accaatcacc    7158
acaatttgtt tctcctcttt atctaagngt tttggccagg ttaaaagcat atatcactat    7218
gttccaagca aacatcggca atggacacgt caaaaataaa tgatcaattg tttcttttgag   7278 tacaaaattg acaatggaca ctatgttcct ttgttagaat tctatttgtc agggtaggat    7338
gtagaaaaac ttaactttta gaggaagctt aaatatccgg cataaacttg cttttttcagc   7398 gctctataaa ataattcaac agtgaattgt ccatcttttc taagtgctcc aaaagacact    7458
aagttgaaaa accaggtgaa ccaacagatt gatccacaaa atcttattat tagattattc    7518
acttaaaagc ctgtctttat ttcaaacata taaaaacaga agttattaat cagggaagcg    7578
cttatggcag cctgagcgaa ccagtgatag caagtggtga aaacagtaaa taggatacat    7638
aaaaattata caaggtttct actgtttatc gaaaaaaaat atttgaaaac agtaaatagg    7698
atacataatc gacttccaac ttgtccttat cataacatcc agaatcacaa caagaattgc    7758
aacgaataca tagtcgactt gagctaagaa gtcacaagac ctgtcaaagt aagctgccct    7818
tgatcttgaa gtgaaaggca tatttttattg tcttccttgg caaacagata tcactgtctt    7878
cagcagttca gttagataat ccaagatttc tcacggagaa gagcatatca ctcacatcag    7938
tgttgtgccc tccaaatact gagataaact gaattttgtt ctctttgaag catctgcagg    7998
cattaacaat aataatactt tacaaagttt cattgggtct aaactattgt ttgcacatca    8058
tatatatgcc cagaactttt tagcatgata caagggtcct gttcataact catgcctaaa    8118
tctgacaaat ttgtcaaacg acaatataag tcgaattata atgcgtttta gaattgacgc    8178
caaaactttt gctagcgtaa gtaactcttc cacctcccag catgcataca accaacaagc    8238
taaacttttg ttcaaaaaaa tgtacattta tttccttgaa cacagccttt gtagaatatg    8298
attaaaaact catggatgaa tgaaataatg taaaagaatg gtcaaaatga tgaatagtac    8358
aagaagcaac tgtgaacatt tcacctttac ctgactgttc gcaagaaggc cacgtggcag    8418
aaaagccaga aatgcaagaa gcttccctaa ttgatacacc atcaagaaat caatggactc    8478
aacaccagcg tccgcccaga caaatgaat gcaggcacct aaaatataga accattgact    8538
tttcaacact gaattatata acctgaatat cttgttttgt taacacatct gacaaaatca    8598
gtgcattctg ttccatatag atgtatgcat agctcccata tgttagttga tcgatgagca    8658
tgcaaactat acacaccta cgttactccc tctgtcaaaa aaatataag cttgtctaga    8718 tacatagcta caaatgctta tattttggaa ttctcttaaa gctgtagaaa cttttatcgc    8778
cccgccatgg caagtcgagc tgccatcccc aatgaaagcc cccacacagg tttcatgccc    8838
tgctgcacaa tattgagcaa ccaaaaatat aataatattt gtgtcagaat ttgaatcaac    8898
cttacagata ctgggtggcc agaaaatcta gtccaagtaa tatcctgaaa aatagcaact    8958
ggcaaatact aaaggcagtg aagagtttcc tttagatcag atgataaaaa aaaatcatat    9018
gttcaatagc aataatcact cacatttttt ttgctgttta gaatttagat aaatagtagt    9078
taaacttcta tagcttgcgt agctaagatc aatggtgatt attagttgaa aaaataatca    9138
aatcatcaaa ctgaggagac ttatacctgc cataagttct gaaatttcaa tgatcctagt    9198
```

-continued

```
caatatttac tgtatatata gaattaggtc caaaagatga tacttacaat taaggatgtt     9258
gtattgatcg gttcataact caagcttcta tttatcatta atcaaaagct ggatcattca     9318
tgcatatacc tttgccgcac tcaacatagc agctcggagt cttctttgtt cagaagcgag     9378
gaaggagtca acaaataagt actgcaatgt taaacaaacc gacatatcaa atcccaaatt     9438
aagaatgcat gatttattaa tacaggaaat atatgatcaa gtcccaaaaa gtgagtcatg     9498
ttatgtacac tcagtcatca atttcaataa gaatattaac ttgctcattg gtatatggat     9558
ttgattatga cataatttga caatacattt acagaataaa cttgcagtgc tgtgagcata     9618
tgttactaac atgtaaggac cttgttttgc tctgttcaat actcatgttg atcttgatct     9678
gtgtccacat atacctaaat gaatgaaat caaagaatga ggtttgtagg agtggagttg      9738
gtgaattata gggtagataa tgtcggcaca accgtttgat aagtagtacg agtactttat     9798
ttggcgccac cgcgccagca tcagatgtgt ggcctttgca ctgattgaac ccaaaagaaa     9858 aaaaaagtc gttttggtcc cacacaattc tacttcatct gcaggatgta cagaaggtta     9918
catatctatt ctgttctatg ctctgtttac atttataagg gctcacttgg tggctgtcat     9978
tggttggctg gtgcggtata ttactaatag gttttttaat ggcatatatg ttcttaaaat    10038
aaaccagaaa agcaaaagat caactatctt agccacacca atgaaatgga atatactgaa    10098
ctgtcacggc taaaattctc ttcagtcacc tggcccagct ggagccgtgg gctcgtcgtc    10158
ttttctaaac atgtactagt attttggggg cccacagtga atttggccca aaatgctgac    10218
agccgctcta cggctctacg ctgtgcag at  ggg cgg ttc atg atg cgg ctg       10269
                                Tyr Gly Arg Phe Met Met Arg Leu
                                                140 aag ctg cca aac ggt gtg acg acg agc gag cag acg agg tac ctg gcg      10317
Lys Leu Pro Asn Gly Val Thr Thr Ser Glu Gln Thr Arg Tyr Leu Ala
145                 150                 155                 160 agc gtg atc gag gcg tac ggc aag gag ggc tgc gcc gac gtg aca acc      10365
Ser Val Ile Glu Ala Tyr Gly Lys Glu Gly Cys Ala Asp Val Thr Thr
                165                 170                 175 cgc cag aac tgg cag atc cgc ggc gtc acg ctc ccc gac gtg ccg gcc      10413
Arg Gln Asn Trp Gln Ile Arg Gly Val Thr Leu Pro Asp Val Pro Ala
            180                 185                 190 atc ctc gac ggg ctc aac gcc gtc ggc ctc acc agc ctc cag agc ggc      10461
Ile Leu Asp Gly Leu Asn Ala Val Gly Leu Thr Ser Leu Gln Ser Gly
        195                 200                 205 atg gac aac gtc cgc aac ccc gtc ggc aac ccg ctc gcc ggc atc gac      10509
Met Asp Asn Val Arg Asn Pro Val Gly Asn Pro Leu Ala Gly Ile Asp
    210                 215                 220 ccc gac gag atc gtc gac acg cga tcc tac acc aac ctc ctc tcc tcc      10557
Pro Asp Glu Ile Val Asp Thr Arg Ser Tyr Thr Asn Leu Leu Ser Ser
225                 230                 235                 240 tac atc acc agc aac ttc cag ggc aac ccc acc atc acc aac ct           10601
Tyr Ile Thr Ser Asn Phe Gln Gly Asn Pro Thr Ile Thr Asn Leu
                245                 250 gtgagtgatc gaatcaactt gatcatgctc tgtgctgtgc tgttcgtgtc gtctctgacg    10661
acatgtttgt tgaatttgtt gttgctgcgt gctgttggca g g ccg agg aag tgg      10715
                                              Pro Arg Lys Trp aac gtg tgc gtg atc ggg tcg cac gat ctg tac gag cac ccg cac atc      10763
Asn Val Cys Val Ile Gly Ser His Asp Leu Tyr Glu His Pro His Ile
260                 265                 270                 275 aac gac ctc gcg tac atg ccg gcg gtg aag ggc ggc aag ttc ggg ttc      10811
Asn Asp Leu Ala Tyr Met Pro Ala Val Lys Gly Gly Lys Phe Gly Phe
                280                 285                 290
```

-continued

```
aac ctc ctt gtc ggc ggg ttc atc agc ccc aag agg tgg gag gag gcg      10859
Asn Leu Leu Val Gly Gly Phe Ile Ser Pro Lys Arg Trp Glu Glu Ala
            295                 300                 305 ctg ccg ctg gac gcc tgg gtc ccc ggc gac gac atc atc ccg gtg tgc      10907
Leu Pro Leu Asp Ala Trp Val Pro Gly Asp Asp Ile Ile Pro Val Cys
        310                 315                 320 aag gcc gtt ctc gag gcg tac cgc gac ctc ggc acc agg ggc aac cgc      10955
Lys Ala Val Leu Glu Ala Tyr Arg Asp Leu Gly Thr Arg Gly Asn Arg
    325                 330                 335 cag aag acc cgc atg atg tgg ctc atc gac gaa ctt gtgagcctcc           11001
Gln Lys Thr Arg Met Met Trp Leu Ile Asp Glu Leu
340                 345                 350 attcatccac gccattgact gaattacgta tgtcccaatg ttcttatcag ttaattgcgg    11061
tgttggcatt gcag gga atg gag gct ttt cgg tcg gag gtg gag aag agg      11111
              Gly Met Glu Ala Phe Arg Ser Glu Val Glu Lys Arg
                          355                 360 atg ccg aac ggc gtg ctg gag cgc gct gcg ccg gac gac ctc atc gac      11159
Met Pro Asn Gly Val Leu Glu Arg Ala Ala Pro Asp Asp Leu Ile Asp
    365                 370                 375 aag aaa tgg cag agg agg gac tac ctc ggc gtg cac ccg cag aag cag      11207
Lys Lys Trp Gln Arg Arg Asp Tyr Leu Gly Val His Pro Gln Lys Gln
380                 385                 390                 395 gaa ggg atg tcc tac gtc ggc ctg cac gtg ccc gtc ggc cgg gtg cag      11255
Glu Gly Met Ser Tyr Val Gly Leu His Val Pro Val Gly Arg Val Gln
            400                 405                 410 gcg gcg gac atg ttc gag ctc gcc cgc ctt gcc gac gag tat ggc tcc      11303
Ala Ala Asp Met Phe Glu Leu Ala Arg Leu Ala Asp Glu Tyr Gly Ser
        415                 420                 425 ggc gag ctc cgc ctc acc gtg gag cag aac atc gtg atc ccg aac gtc      11351
Gly Glu Leu Arg Leu Thr Val Glu Gln Asn Ile Val Ile Pro Asn Val
    430                 435                 440 aag aac gag aag gtg gag gcg ctg ctc gcc gag ccg ctg ctt cag aag      11399
Lys Asn Glu Lys Val Glu Ala Leu Leu Ala Glu Pro Leu Leu Gln Lys
445                 450                 455 ttc tcc ccg cag ccg tcg ctg ctc aag ggc ctg gtc gcg tgc acc          11447
Phe Ser Pro Gln Pro Ser Leu Leu Leu Lys Gly Leu Val Ala Cys Thr
460                 465                 470                 475 ggc aac cag ttc tgc ggc cag gcc atc atc gag acg aag cag cgg gcg      11495
Gly Asn Gln Phe Cys Gly Gln Ala Ile Ile Glu Thr Lys Gln Arg Ala
            480                 485                 490 ctg ctg gtg acg tcg cag gtg gag aag ctc gtg tcg gtg ccc cgg gcg      11543
Leu Leu Val Thr Ser Gln Val Glu Lys Leu Val Ser Val Pro Arg Ala
        495                 500                 505 gtg cgg atg cac tgg acc ggc tgc ccc aac agc tgc ggc cag gtg cag      11591
Val Arg Met His Trp Thr Gly Cys Pro Asn Ser Cys Gly Gln Val Gln
    510                 515                 520 gtc gcc gac atc ggc ttc atg ggc tgc ctc acc aag gat agc gcc ggc      11639
Val Ala Asp Ile Gly Phe Met Gly Cys Leu Thr Lys Asp Ser Ala Gly
525                 530                 535 aag atc gtc gag gcg gcc gac atc ttc gtc ggc ggc cgc gtc ggc agc      11687
Lys Ile Val Glu Ala Ala Asp Ile Phe Val Gly Gly Arg Val Gly Ser
540                 545                 550                 555 gac tcg cac ctc gcc ggc gcg tac aag aag tcc gtg ccg tgc gac gag      11735
Asp Ser His Leu Ala Gly Ala Tyr Lys Lys Ser Val Pro Cys Asp Glu
            560                 565                 570 ctg gcg ccg atc gtc gcc gac atc ctg gtc gag cgg ttc ggg gcc gtg      11783
Leu Ala Pro Ile Val Ala Asp Ile Leu Val Glu Arg Phe Gly Ala Val
        575                 580                 585
```

-continued

```
cgg agg gag agg gag gag gac gag gag tag gagcacagac tggggtggtt         11833
Arg Arg Glu Arg Glu Glu Asp Glu Glu
        590                 595 tgcttgctcc ggtgatctct cgccgtcctt gtaaagtaga cgacaatatg ccttcgccca      11893
tggcacgctt gtactgtcac gttttggttt gatcttgtag cccaaaagtt gtgttcattc      11953
tcgttacagt cttacagagg atgattgatt gataaataaa naagaaacag attctgcaac      12013
tgttcatcgc tgttcctaaa tctgatttcg cgatagtatc ttgtctgacc tgtcccaatc      12073
gcagtgctaa aaccatataa tcttgcaagc aaatgaaatt gaaagagttc aatgcaacca      12133
ctaacggtct aacaacatga taaggcct                                         12161

<210> SEQ ID NO 2
<211> LENGTH: 2519
<212> TYPE: DNA
<213> ORGANISM: Oryza sativa
<220> FEATURE:
<221> NAME/KEY: CDS
<222> LOCATION: (532)..(2322)
<223> OTHER INFORMATION:

<400> SEQUENCE: 2
tatctccttc tctctcgtcg cttttctgcgt ctccccgtct ctccttcgcc aacagccgag       60
aagaggcaga gagagcgccg cccccccgtcc ctctctctcc ctctcgtcct cgcccccatc      120
cctctcgtct ttcccttgcc ggcagcagag gaggcggcag cgacggcttc agctgctccc      180
acgggccgga tcgggcagtg gcggtggcgt cggcggcttc cgctggcgaa tccggcgggt      240
gaatcgggtg aaatttgggt gaccccgat acaaatcagt gttccgatag gtaatacccct     300 gctctcagca tctgccctt tgaattcgcc aagagccagc atctgccctt ttgaattcgc      360
caagggccag catctgccca tttgattttg aattcgccaa gagccagcaa cagcgccccc      420 gcgcccctc cctcctccgc aataaacagc cacacgcgcc gccccatgt ccaccctcat       480 cgccacagcg caccaccacc accaccacca ccaccaccac cgtctccagc c atg gcc      537
                                                         Met Ala
                                                           1 tcc tcc gcc tcc ctg cag cgc ttc ctc ccc ccg tac ccc cac gcg gca      585
Ser Ser Ala Ser Leu Gln Arg Phe Leu Pro Pro Tyr Pro His Ala Ala
      5                  10                  15 gca tcc cgc tgc cgc cct ccc ggc gtc cgc gcc cgc ccc gtg cag tcg      633
Ala Ser Arg Cys Arg Pro Pro Gly Val Arg Ala Arg Pro Val Gln Ser
 20                  25                  30 tcg acg gtg tcc gca ccg tcc tcc tcg act ccg gcg gcg gac gag gcc      681
Ser Thr Val Ser Ala Pro Ser Ser Ser Thr Pro Ala Ala Asp Glu Ala
 35                  40                  45                  50 gtg tcg gcg gag cgg ctg gag ccg cgg gtg gag cag cgg gag ggc cgg      729
Val Ser Ala Glu Arg Leu Glu Pro Arg Val Glu Gln Arg Glu Gly Arg
              55                  60                  65 tac tgg gtg ctc aag gag aag tac cgg acg ggg ctg aac ccg cag gag      777
Tyr Trp Val Leu Lys Glu Lys Tyr Arg Thr Gly Leu Asn Pro Gln Glu
         70                  75                  80 aag gtg aag ctg ggg aag gag ccc atg tca ttg ttc atg gag ggc ggc      825
Lys Val Lys Leu Gly Lys Glu Pro Met Ser Leu Phe Met Glu Gly Gly
     85                  90                  95 atc aag gag ctc gcc aag atg ccc atg gag gag atc gag gcc gac aag      873
Ile Lys Glu Leu Ala Lys Met Pro Met Glu Glu Ile Glu Ala Asp Lys
100                 105                 110 ctc tcc aag gag gac atc gac gtg cgg ctc aag tgg ctc ggc ctc ttc      921
Leu Ser Lys Glu Asp Ile Asp Val Arg Leu Lys Trp Leu Gly Leu Phe
115                 120                 125                 130
```

-continued

```
cac cgc cgc aag cat cag tat ggg cgg ttc atg atg cgg ctg aag ctg       969
His Arg Arg Lys His Gln Tyr Gly Arg Phe Met Met Arg Leu Lys Leu
                135                 140                 145 cca aac ggt gtg acg acg agc gag cag acg agg tac ctg gcg agc gtg      1017
Pro Asn Gly Val Thr Thr Ser Glu Gln Thr Arg Tyr Leu Ala Ser Val
            150                 155                 160 atc gag gcg tac ggc aag gag ggc tgc gcc gac gtg aca acc cgc cag      1065
Ile Glu Ala Tyr Gly Lys Glu Gly Cys Ala Asp Val Thr Thr Arg Gln
        165                 170                 175 aac tgg cag atc cgc ggc gtc acg ctc ccc gac gtg ccg gcc atc ctc      1113
Asn Trp Gln Ile Arg Gly Val Thr Leu Pro Asp Val Pro Ala Ile Leu
    180                 185                 190 gac ggg ctc aac gcc gtc ggc ctc acc agc ctc cag agc ggc atg gac      1161
Asp Gly Leu Asn Ala Val Gly Leu Thr Ser Leu Gln Ser Gly Met Asp
195                 200                 205                 210 aac gtc cgc aac ccc gtc ggc aac ccg ctc gcc ggc atc gac ccc gac      1209
Asn Val Arg Asn Pro Val Gly Asn Pro Leu Ala Gly Ile Asp Pro Asp
                215                 220                 225 gag atc gtc gac acg cga tcc tac acc aac ctc ctc tcc tcc tac atc      1257
Glu Ile Val Asp Thr Arg Ser Tyr Thr Asn Leu Leu Ser Ser Tyr Ile
            230                 235                 240 acc agc aac ttc cag ggc aac ccc acc atc acc aac ctg ccg agg aag      1305
Thr Ser Asn Phe Gln Gly Asn Pro Thr Ile Thr Asn Leu Pro Arg Lys
        245                 250                 255 tgg aac gtg tgc gtg atc ggg tcg cac gat ctg tac gag cac ccg cac      1353
Trp Asn Val Cys Val Ile Gly Ser His Asp Leu Tyr Glu His Pro His
    260                 265                 270 atc aac gac ctc gcg tac atg ccg gcg gtg aag ggc ggc aag ttc ggg      1401
Ile Asn Asp Leu Ala Tyr Met Pro Ala Val Lys Gly Gly Lys Phe Gly
275                 280                 285                 290 ttc aac ctc ctt gtc ggc ggg ttc atc agc ccc aag agg tgg gag gag      1449
Phe Asn Leu Leu Val Gly Gly Phe Ile Ser Pro Lys Arg Trp Glu Glu
                295                 300                 305 gcg ctg ccg ctg gac gcc tgg gtc ccc ggc gac gac atc atc ccg gtg      1497
Ala Leu Pro Leu Asp Ala Trp Val Pro Gly Asp Asp Ile Ile Pro Val
            310                 315                 320 tgc aag gcc gtt ctc gag gcg tac cgc gac ctc ggc acc agg ggc aac      1545
Cys Lys Ala Val Leu Glu Ala Tyr Arg Asp Leu Gly Thr Arg Gly Asn
        325                 330                 335 cgc cag aag acc cgc atg atg tgg ctc atc gac gaa ctt gga atg gag      1593
Arg Gln Lys Thr Arg Met Met Trp Leu Ile Asp Glu Leu Gly Met Glu
    340                 345                 350 gct ttt cgg tcg gag gtg gag aag agg atg ccg aac ggc gtg ctg gag      1641
Ala Phe Arg Ser Glu Val Glu Lys Arg Met Pro Asn Gly Val Leu Glu
355                 360                 365                 370 cgc gct gcg ccg gac gac ctc atc gac aag aaa tgg cag agg agg gac      1689
Arg Ala Ala Pro Asp Asp Leu Ile Asp Lys Lys Trp Gln Arg Arg Asp
                375                 380                 385 tac ctc ggc gtg cac ccg cag aag cag gaa ggg atg tcc tac gtc ggc      1737
Tyr Leu Gly Val His Pro Gln Lys Gln Glu Gly Met Ser Tyr Val Gly
            390                 395                 400 ctg cac gtg ccc gtc ggc cgg gtg cag gcg gcg gac atg ttc gag ctc      1785
Leu His Val Pro Val Gly Arg Val Gln Ala Ala Asp Met Phe Glu Leu
        405                 410                 415 gcc cgc ctt gcc gac gag tat ggc tcc ggc gag ctc cgc ctc acc gtg      1833
Ala Arg Leu Ala Asp Glu Tyr Gly Ser Gly Glu Leu Arg Leu Thr Val
    420                 425                 430 gag cag aac atc gtg atc ccg aac gtc aag aac gag aag gtg gag gcg      1881
Glu Gln Asn Ile Val Ile Pro Asn Val Lys Asn Glu Lys Val Glu Ala
```

-continued

```
                435                 440                 445                 450
ctg ctc gcc gag ccg ctg ctt cag aag ttc tcc ccg cag ccg tcg ctg           1929
Leu Leu Ala Glu Pro Leu Leu Gln Lys Phe Ser Pro Gln Pro Ser Leu
                455                 460                 465 ctg ctc aag ggc ctg gtc gcg tgc acc ggc aac cag ttc tgc ggc cag           1977
Leu Leu Lys Gly Leu Val Ala Cys Thr Gly Asn Gln Phe Cys Gly Gln
        470                 475                 480 gcc atc atc gag acg aag cag cgg gcg ctg ctg gtg acg tcg cag gtg           2025
Ala Ile Ile Glu Thr Lys Gln Arg Ala Leu Leu Val Thr Ser Gln Val
                485                 490                 495 gag aag ctc gtg tcg gtg ccc cgg gcg gtg cgg atg cac tgg acc ggc           2073
Glu Lys Leu Val Ser Val Pro Arg Ala Val Arg Met His Trp Thr Gly
        500                 505                 510 tgc ccc aac agc tgc ggc cag gtg cag gtc gcc gac atc ggc ttc atg           2121
Cys Pro Asn Ser Cys Gly Gln Val Gln Val Ala Asp Ile Gly Phe Met
515                 520                 525                 530 ggc tgc ctc acc aag gac agc gcc ggc aag atc gtc gag gcg gcc gac           2169
Gly Cys Leu Thr Lys Asp Ser Ala Gly Lys Ile Val Glu Ala Ala Asp
            535                 540                 545 atc ttc gtc ggc ggc cgc gtc ggc agc gac tcg cac ctc gcc ggc gcg           2217
Ile Phe Val Gly Gly Arg Val Gly Ser Asp Ser His Leu Ala Gly Ala
        550                 555                 560 tac aag aag tcc gtg ccg tgc gac gag ctg gcg ccg atc gtc gcc gac           2265
Tyr Lys Lys Ser Val Pro Cys Asp Glu Leu Ala Pro Ile Val Ala Asp
                565                 570                 575 atc ctg gtc gag cgg ttc ggg gcc gtg cgg agg gag agg gag gag gac           2313
Ile Leu Val Glu Arg Phe Gly Ala Val Arg Arg Glu Arg Glu Glu Asp
        580                 585                 590 gag gag tag gagcacagac tggggtggtt tgcttgctcc ggtgatctct                   2362
Glu Glu
595 cgccgtcctt gtaaagtaga cgacaatatg ccttcgccca tggcacgctt gtactgtcac         2422 gttttggttt gatcttgtag cccaaaagtt gtgttcattc tcgttacagt cttacagagg         2482 atgattgatt gataaataaa gaagaaacag attctgc                                  2519
```

<210> SEQ ID NO 3
<211> LENGTH: 596
<212> TYPE: PRT
<213> ORGANISM: Oryza sativa

<400> SEQUENCE: 3

Met Ala Ser Ser Ala Ser Leu Gln Arg Phe Leu Pro Pro Tyr Pro His
1               5                   10                  15

Ala Ala Ala Ser Arg Cys Arg Pro Pro Gly Val Arg Ala Arg Pro Val
            20                  25                  30

Gln Ser Ser Thr Val Ser Ala Pro Ser Ser Thr Pro Ala Ala Asp
        35                  40                  45

Glu Ala Val Ser Ala Glu Arg Leu Glu Pro Arg Val Glu Gln Arg Glu
    50                  55                  60

Gly Arg Tyr Trp Val Leu Lys Glu Lys Tyr Arg Thr Gly Leu Asn Pro
65                  70                  75                  80

Gln Glu Lys Val Lys Leu Gly Lys Glu Pro Met Ser Leu Phe Met Glu
                85                  90                  95

Gly Gly Ile Lys Glu Leu Ala Lys Met Pro Met Glu Glu Ile Glu Ala
            100                 105                 110

Asp Lys Leu Ser Lys Glu Asp Ile Asp Val Arg Leu Lys Trp Leu Gly
        115                 120                 125

```
Leu Phe His Arg Arg Lys His Gln Tyr Gly Arg Phe Met Met Arg Leu
    130                 135                 140

Lys Leu Pro Asn Gly Val Thr Thr Ser Glu Gln Thr Arg Tyr Leu Ala
145                 150                 155                 160

Ser Val Ile Glu Ala Tyr Gly Lys Glu Gly Cys Ala Asp Val Thr Thr
            165                 170                 175

Arg Gln Asn Trp Gln Ile Arg Gly Val Thr Leu Pro Asp Val Pro Ala
                180                 185                 190

Ile Leu Asp Gly Leu Asn Ala Val Gly Leu Thr Ser Leu Gln Ser Gly
            195                 200                 205

Met Asp Asn Val Arg Asn Pro Val Gly Asn Pro Leu Ala Gly Ile Asp
    210                 215                 220

Pro Asp Glu Ile Val Asp Thr Arg Ser Tyr Thr Asn Leu Leu Ser Ser
225                 230                 235                 240

Tyr Ile Thr Ser Asn Phe Gln Gly Asn Pro Thr Ile Thr Asn Leu Pro
            245                 250                 255

Arg Lys Trp Asn Val Cys Val Ile Gly Ser His Asp Leu Tyr Glu His
                260                 265                 270

Pro His Ile Asn Asp Leu Ala Tyr Met Pro Ala Val Lys Gly Gly Lys
            275                 280                 285

Phe Gly Phe Asn Leu Leu Val Gly Gly Phe Ile Ser Pro Lys Arg Trp
290                 295                 300

Glu Glu Ala Leu Pro Leu Asp Ala Trp Val Pro Gly Asp Asp Ile Ile
305                 310                 315                 320

Pro Val Cys Lys Ala Val Leu Glu Ala Tyr Arg Asp Leu Gly Thr Arg
            325                 330                 335

Gly Asn Arg Gln Lys Thr Arg Met Met Trp Leu Ile Asp Glu Leu Gly
                340                 345                 350

Met Glu Ala Phe Arg Ser Glu Val Glu Lys Arg Met Pro Asn Gly Val
            355                 360                 365

Leu Glu Arg Ala Ala Pro Asp Asp Leu Ile Asp Lys Lys Trp Gln Arg
    370                 375                 380

Arg Asp Tyr Leu Gly Val His Pro Gln Lys Gln Glu Gly Met Ser Tyr
385                 390                 395                 400

Val Gly Leu His Val Pro Val Gly Arg Val Gln Ala Ala Asp Met Phe
            405                 410                 415

Glu Leu Ala Arg Leu Ala Asp Glu Tyr Gly Ser Gly Glu Leu Arg Leu
                420                 425                 430

Thr Val Glu Gln Asn Ile Val Ile Pro Asn Val Lys Asn Glu Lys Val
            435                 440                 445

Glu Ala Leu Leu Ala Glu Pro Leu Leu Gln Lys Phe Ser Pro Gln Pro
    450                 455                 460

Ser Leu Leu Leu Lys Gly Leu Val Ala Cys Thr Gly Asn Gln Phe Cys
465                 470                 475                 480

Gly Gln Ala Ile Ile Glu Thr Lys Gln Arg Ala Leu Leu Val Thr Ser
            485                 490                 495

Gln Val Glu Lys Leu Val Ser Val Pro Arg Ala Val Arg Met His Trp
                500                 505                 510

Thr Gly Cys Pro Asn Ser Cys Gly Gln Val Gln Val Ala Asp Ile Gly
            515                 520                 525

Phe Met Gly Cys Leu Thr Lys Asp Ser Ala Gly Lys Ile Val Glu Ala
    530                 535                 540
```

-continued

```
Ala Asp Ile Phe Val Gly Gly Arg Val Gly Ser Asp Ser His Leu Ala
545                 550                 555                 560

Gly Ala Tyr Lys Lys Ser Val Pro Cys Asp Glu Leu Ala Pro Ile Val
                565                 570                 575

Ala Asp Ile Leu Val Glu Arg Phe Gly Ala Val Arg Arg Glu Arg Glu
            580                 585                 590

Glu Asp Glu Glu
        595

<210> SEQ ID NO 4
<211> LENGTH: 12179
<212> TYPE: DNA
<213> ORGANISM: Oryza sativa
<220> FEATURE:
<221> NAME/KEY: exon
<222> LOCATION: (6001)..(6409)
<223> OTHER INFORMATION:
<220> FEATURE:
<221> NAME/KEY: exon
<222> LOCATION: (10255)..(10609)
<223> OTHER INFORMATION:
<220> FEATURE:
<221> NAME/KEY: exon
<222> LOCATION: (10712)..(11000)
<223> OTHER INFORMATION:
<220> FEATURE:
<221> NAME/KEY: exon
<222> LOCATION: (11094)..(11831)
<223> OTHER INFORMATION:

<400> SEQUENCE: 4
```

| | | | | | |
|---|---|---|---|---|---|
| ctcgagcttt | tttgactgcc | ctaatcaggc | gggttccttg | tgggacccac | ataatgcttt | 60 |
| ttttaatcgc | cttcacgggc | tgcatgcaaa | ctatacggcg | tggtacttcc | actactagaa | 120 |
| aaaacgggct | tttcgcaggc | gggcaaacct | tccgcatgta | tattaacgac | cgtaaaaatc | 180 |
| tccaattttc | acaggtggac | cccagcaccg | cctgcgaaaa | taattttcgc | aggctgcatt | 240 |
| tcgaatcttc | ctgggtgcta | cagtaaacca | cctgcgaaaa | tactcacggc | gccaaaaaaa | 300 |
| aaatttccgc | cagccccgcc | ccctccctat | tcaaatcaca | aattctcaca | aatctcatcc | 360 |
| aaaaacaaaa | ttcaatccaa | aaatccatac | atcaacacaa | agcattggat | tcaaatccac | 420 |
| aacatcaatt | tacaagttaa | catcaatcaa | catgtaagct | ttaaaacgaa | acgtcgtcgt | 480 |
| cgccggcaaa | ctccttttgc | atgcggtgcc | gccgccgccc | ccctccccccc | tctgtccgga | 540 |
| tttgggaggg | agggaggtgt | tgccgccac | caccgccctc | ccctctcctc | gtagggccgg | 600 |
| atctcgggag | ggaggagagg | ggagccgcct | ccgcacagcc | atcaacgtcc | gtgccgccgt | 660 |
| cgcctcgttc | gcaccaccgc | cgttgcttcc | cctcctccgg | ccagatctag | gagcggggag | 720 |
| gaagagaggg | ggagccaccg | ccaccgtcgc | ccctcgcgt | ccgcgccgtc | gtcaccgtcc | 780 |
| acgccgccgc | gtccgtgccg | ccgctgtcgc | tccccctcct | ctggcgagga | gggagagaga | 840 |
| gggagccgtc | gcgccgccgt | cgctcccctc | cttcggcgag | gagggagaga | ggggaggga | 900 |
| agagggatgg | agggaggag | agtggcgctg | agagagagag | agagagacgc | tgaggagagg | 960 |
| aaatgagtgg | tggggagggg | tggaggagaa | gataaggagg | acttagattt | ttttttttggg | 1020 |
| taagtatgat | ttttgcaggc | ggaccacata | aggttccgcc | tgcgaaaatc | aattttttcg | 1080 |
| cgcagaccac | ttaagaggtc | cgcatgcgaa | aataaaggta | ttttttttagg | cggacctctt | 1140 |
| aagtggtccg | cctggaaaaa | ttgattttcg | caagcggatg | acgaaaattc | accccggttt | 1200 |
| atattttcga | agatgcttca | tcgacgacat | cgactgcgtc | ctctatgaca | gcaacgaccg | 1260 |
| cgtcaccgac | gacggcatcg | atcacgtcat | ctacgatgac | aatgactgca | tcaactccgc | 1320 |

```
atcactattg tgatgactgt tacacggcgt agaagaacca accaaagtgg tggcttcatc    1380
gccaacgacg tcctctaaca tatgcaagac gtccccaatg gcatcctctg acatctacaa    1440
ggtgcaagat gctaacaatt acagttttg tcttcacact gtggcataaa tatttttttt    1500
caccttcggc tatatgcggc tacacctaca accacggtta ctacatgatc ggctccatca    1560
acgaacatct ataacaacaa tcattgatgg aaactctagt caaagcgtct gtgtcatcgc    1620
tatcatccat gacactcccg ctatgactac gtgagggaat agataagagt caagggacga    1680
cacggaagga gacgtaggca ccaggtggag gaccatccat caaagatgca attgatgatg    1740
gtgagttgaa aagatgaag aaataaaata tttcaaatcc agtcgcaatc attcgcttcg    1800
ctcccgttac gactgagggg gaatgttaga agcatagata tattaattgg agataagagt    1860
catacaaata tagagataag atatcatcct agagatagaa tcctagagat aaaatatagt    1920
cctagagata aatctactct tacttgtacc cctatatata ccccatgaga ggatcaatgc    1980
aatacaccga gaatacaaca attagatttt tctacggttg taactataat acgctgtaat    2040
atgctggatc ggggaagagc gcccgtaatc agtgccccag agatgtaggt ctcggttgaa    2100
ctccattatc aaataccgta cctcggtgtc gtcatcatgt ttgaatcttc tatgacgttt    2160
cttttgcatt cggttttcga tgtgacttcg gggctggttt tataacaatg attatagtgc    2220
tgttgacggc aatcggttgt gagaattagc tattcgggtc cctccatgtg atttctttgt    2280
gattgggatg tatggtaatg ctagggtttt aaggtgtagg attggtgcat gagagatcat    2340
cacttcactt gtatgacctt ctctcctttt atatttttt atcattctct ccttttttt    2400 ataatgctac tgaactagtg gaatacaggg gactaatgca aaataaaaga aaagtatcac    2460
tggtcacggc atataattta gaaagtgtgt gatttaggca tagggctgac catgacccct    2520
tacgacttgg tcgctcggtt tgttagacga tagatcaacc aacaaaagct acgatacatg    2580
atgtacgtgt caggatacaa atccttacaa ataacaacag ttattgttcg ataactatca    2640
gttgtctagg cttaccaatg tataatagaa gatgaaaatt ccatattact ggtatcgttc    2700
aatgctagta actctttgag ctttgtctag gttaaaaaaa aaattatgga tccaccatca    2760
caaaaatgaa aaacaccggg gaaaacaaaa aaccatttga tagcagcaca agacaaaatg    2820
atgttaccgt ctacccgagc tcctactccg taccagcaca accaaacgaa cagtacccgc    2880
cggaccaggg gcacgttcgt aaatttccct cccgtggctg gctggctgcc atctctctca    2940
accagggttg gtaatttcgg ccgtttcggt gggtcccgat agtaaatgag ctccggtcaa    3000
aacgccctcc gcctcccctc attgcgccgc acgcacaccg catctagatc cagatcgaaa    3060
aaatcgctat ctcgccgagt cgccagtcac cgcctcgacg ccggtcgccg taccgccggc    3120
gctgcacgcc cccctccaag ccgtcgcccc atcgccccca gccgcccagt ggtggggcgg    3180
cggatgccga gcttggcgag gttgccgagg acgaaccagg cgaggaggac gaggatcttg    3240
tcgacgagcc agagcgggag ccacgccatg agcaacacgg cgagctcgaa cgtggacttg    3300
ccgagcacct cgccagggag gacgtggacg gcgtcgcgca ccaccatcgc cgggagggcg    3360
ctgtggtcgc acaggtcgag cgacaccacc atgccggagt tgccgcaccc gacgacgagc    3420
accttcttgc cgcggtacgc ctcgccggac ttgtagaccg cgacatgcat cacctcgctg    3480
ctatatttgt tcttggactg tggagacttg ctgtcagtgg gtgtgttcag aattgctgct    3540
gcagcttgca gcgaatttgt gatgcagcag ctgcagcttg tatggctgcc gagtagagcg    3600
agtgttgcta tctgttttg ttctcttttt cagaaatttc gcccgcaaat tttaaatttg    3660
```

```
aattcaaatt tttaaaagaa ctagaaaata tgcccgtgcg ttgcaccggg tgaatatcaa    3720
acaaatattg atgggtaaga ttgcttgtgt acttataaca catatgcaca aaatatattga   3780 atatgtacat acctcgcaaa tatctccaaa ttttatacat atgagttgtg taaatcatgt    3840
gagttccata ttgtcatgtt aatatggagt attactgatg agcccatcta tggtgataat    3900
tttggaggtt gtagctcaac gaatttgtat ttgctatgta tctcaacgtt gataagtcac    3960
tactacaacc atcggcgacc tttctcggga tccaagcatg tcgaccccgc aacgtggcg     4020 tcggtgcagg gcaccgagat gaacaccacg gggctatttg cctgtccagg gtcatcctag    4080
gcttaaggcc acgacactca aggacgtggt aggcggcgtc acagaggtgc tcccagcgaa    4140
caagctggcc accaaggagg acgccgacaa ggtggcggcc accgctatgc agaaacgatg    4200
ggaggcatgc cggtgacgac aaggagctaa cacgatccat ttagtcccga tccgagttta    4260
tcaggaattc aatcctgcac cgtgcggtta cgttttttctt ttccgcggga aaagcaatca   4320
ccgatggtag ggacaaagtg cgtgtgagaa cagaggccag gccaaagtgc gtgcgagaac    4380
ggaggctagg ccatcgctgg attggattta cgaatgaaat atcgatgtga cgaacagaaa    4440
attatcagtt tgatttaatt ttcataatca gaactctttta ataggaaaaa aattacatgt   4500
acgttccttc atcgtgccca tgtccatctg ggagtccagg tttattcaca aagacccaat    4560
caacagccag gaatccatgt ccttccccgc cgttccctac tctgcttttt tttcttttcat   4620 ttgaaacctt ccgctatgaa tttctagtcg ttcctagcat ccacgcacac aaaatagatt    4680
tccctcgcaa ggcaaaacat acaaatatga gtgcatgcaa gatattacaa acccaatcca    4740
ttaaaaatag aaaataatta actttagcct acctatctca atattggtat atgcccaaac    4800
tcaaaaggag aaaaaaccaaa ctaaaacttt aataaaagtg aacccaagag ataaaaaggt   4860
gatagtaaca acaaaatctc acttgacaat gtcgttaatc aacactgtttt ttaaaatatta  4920 cttaaaaatc tttatattta cctattaaaa caatgaaaaa cagaagatgt ttcttttttta   4980 tttacaacag cgttgtattt agtcatgtcc tatctaagag agaaaaatga atttaacgaa    5040
aagaagctca gaaaaaaaaa gagaacaggg ccaccacacc agtaatccct atgttatcaa    5100
tgaaaaaaaa tttcaatgct aggtttttta taagaaaagg tgataaagtg ttgaaaaaat    5160
acagcaggaa attatatatc ttgctggttt aacatgaatt caagcatata gatataaaaa    5220
tatatcaggc taggaaagga aaaggataaa attggagaga aaaaggaaaa gaacagtaga    5280
ggataaccag caaaaagatg aaaggattcg aacccatgac ctagcggtac aattgtttca    5340
caggctaacc aattgagaat catcgacgtt gtgtcatctt gtgtagctac atttgaaaaa    5400
atatgttttg agctgaacgt tggtgtgtcc gccccctgcat ccgatacatg ttggagcgtg   5460
gagcgcggta aagaaaaaat cctatcgaac cttatctcct tctctctcgt cgcttttctgc   5520 gtctccccgt ctctccttcg ccaacagccg agaagaggca gagagagcgc cgcccccccgt   5580 ccctctctct ccctctcgtc ctcgccccca tccctctcgt cttttcccttg ccggcagcag   5640 aggaggcggc agcgacggct tcagctgctc ccacgggccg gatcgggcag tggcggtggc    5700
gtcggcggct tccgctggcg aatccggcgg gtggatacaa atcagtgttc cgataggtaa    5760
aaccctgctc tcagcatctg ccctttttgaa ttcgccaaga ccagcatct gccctttttga   5820 attcgccaag ggccagcatc tgcccatttg attttgaatt cgccaagagc cagcaacagc    5880 gccccccgcgc cccctccctc ctccgcaata acagccaca cgcgccgccc ccatgtccac    5940
cctcatcgcc acagcgcacc accaccacca ccaccaccac caccaccacc gtctccagcc    6000 atg gcc tcc tcc gcc tcc ctg cag cgc ttc ctc ccc ccg tac ccc cac      6048
```

```
Met Ala Ser Ser Ala Ser Leu Gln Arg Phe Leu Pro Pro Tyr Pro His
1               5                   10                  15 gcg gca gca tcc cgc tgc cgc cct ccc ggc gtc cgc gcc cgc ccc gtg      6096
Ala Ala Ala Ser Arg Cys Arg Pro Pro Gly Val Arg Ala Arg Pro Val
                20                  25                  30 cag tcg tcg acg gtg tcc gca ccg tcc tcc tcg act ccg gcg gcg gac      6144
Gln Ser Ser Thr Val Ser Ala Pro Ser Ser Ser Thr Pro Ala Ala Asp
                35                  40                  45 gag gcc gtg tcg gcg gag cgg ctg gag ccg cgg gtg gag cag cgg gag      6192
Glu Ala Val Ser Ala Glu Arg Leu Glu Pro Arg Val Glu Gln Arg Glu
    50                  55                  60 ggc cgg tac tgg gtg ctc aag gag aag tac cgg acg ggg ctg aac ccg      6240
Gly Arg Tyr Trp Val Leu Lys Glu Lys Tyr Arg Thr Gly Leu Asn Pro
65              70                  75                  80 cag gag aag gtg aag ctg ggg aag gag ccc atg tca ttg ttc atg gag      6288
Gln Glu Lys Val Lys Leu Gly Lys Glu Pro Met Ser Leu Phe Met Glu
                85                  90                  95 ggc ggc atc aag gag ctc gcc aag atg ccc atg gag gag atc gag gcc      6336
Gly Gly Ile Lys Glu Leu Ala Lys Met Pro Met Glu Glu Ile Glu Ala
                100                 105                 110 gac aag ctc tcc aag gag gac atc gac gtg cgg ctc aag tgg ctc ggc      6384
Asp Lys Leu Ser Lys Glu Asp Ile Asp Val Arg Leu Lys Trp Leu Gly
            115                 120                 125 ctc ttc cac cgc cgc aag cat cag t gtatgcctct cttctcttgc              6429
Leu Phe His Arg Arg Lys His Gln
130                 135 tcctctgatc aacacatttt cttgctttcg ttcggttatt tgtcgcgccg aggaagttaa    6489
ttcgccaaga tattctgcag ttttttttct cgatgcacat tcagcaacct aattaagact    6549
gattaagttg ctgtgatttt tatagcttaa ttacggtctc gtgggtaatg actatttata    6609
ttgagtaaac atggttacct tgatccaat cacttcacct ccatgtgcca tatatagcca     6669
caggctctac caagtaacac tagtaatatg cctgtgatac gccacggtgg cataataaat    6729
cattaaattt tattataatc aaattaagga tcctaaaatt ggtccaattg ggtgttaatt    6789
cgatgcaggt catataaaaa tatattttag gcaaggtgca attcaagagc atcaaccatt    6849
atatccaatc actttaatat atatttgaag ataacatatg tcggaaaaaa aatgatggag    6909
agctatttca ttaacttgtg agcataaaca gatcaccaga tgatgccacc ataagtcccg    6969
ccacagtaag tgatgcagct catcttgccc taggcgttcg gtctaaccag tagatagaaa    7029
gagtacaaca tagatcgaat gaaaaaaaaa atctccagaa gaaagctcaa ccacattgag    7089
taaattagag caacaatcaa atcgagtcag catatcgtta tgttagcaga accaatcacc    7149
acaatttgtt tctcctcttt atctaagtgt tttgccaggt taaaagcata tatcactatg    7209
ttccaagcaa acatcggcaa tggacatgtc aaaaataaat gatcaattgt ttctttgagt    7269
acaaaattga caatggacac tatgttcctt tgttagaatt ctatttgtca gggtaggatg    7329
tagaaaaact taactttag aggaagctta aatatccggc ataaacttgc ttttcagcg     7389 ctctataaaa taattcaaca gtgaattgtc catcttttct aagtgctcca aaagacacta    7449
agttgaaaaa ccaggtgaac caacagattg atccacaaaa tcttattatt agattattca    7509
cttaaaagcc tgtctttatt tcaaacatat aaaaacagaa gttattaatc agggaagcgc    7569
ttatggcagc ctgagcgaac cagtgatagc aagtggtgaa acagtaaat aggatacata     7629 aaaattatac aaggttccta ctgtttatca aaaaaaaata tttgaaaaca gtaaatagga    7689
tacataatcg acttccaact tgtccttatc ataacatcca gaatcacaac aagaattgca    7749
```

```
acgaatacat agtcgacttg agctaagaag tcacaagacc tgtcaaagta agctgccctt    7809
gatcttgaag tgaaaggcat attttattgt cttccttggc aaacagatat cactgtcttc    7869
agcagttcag ttagataatc caagatttct cacggagaag agcatatcac tcgcatcagt    7929
gttgtgccct ccaaatactg agataaactg aattttgttc tctttgaagc atctgcaggc    7989
attaacaatt ataatacttt acaaagtttc attgggtcta aactattgtt tgcacatcat    8049
atatatgccc agaactttt  agcatgatac aagggtcctg ttcataactc atgcctaaat    8109
ctgacaaatt tgtcaaacga caatataagt cgaattataa tgcgttttag aattgacgcc    8169
aaaactttg  ctagcgtaag taactcttcc acctcccagc atgcatacaa ccaacaagct    8229
aaacttttgt tcaaaaaaat gtacatttat ttccttgaac acagcctttg tagaatatga    8289
ttaaaaactc atggatgaat gaataatgt  aaaagaatgg tcaaaatgat gaatagtaca    8349
agaagcaact gtgaacattt cacctttacc tgactgttcg caagaaggcc acgtggcaga    8409
aaagccagaa atgcaagaag cttccctaat tgatacacca tcaagaaatc aatggactca    8469
acaccagcgt ctgcccagac aaaatgaatg caggcaccta aaatatagaa ccattgactt    8529
ttcaacactg aattatataa cctgaatatc ttgttttttt aacacatctg acaaaatcag    8589
tgcattctgt tccatataga tgtatgcata gctcccatat gttagttgat cgatgagcat    8649
gcaaactata cacccttac  gttactccct ctgtcaaaaa aatataagc  ttgtctagat    8709
acatagctac aaatgcttat attttggat  tctcttaaag ctgtagaaac ttttatcgcc    8769
ccgccatggc aagtcgagat gccatcccca atgaaagccc ccacacaggt ttcatgccct    8829
gctgcacaat attgagcaac caaaaatata ataatatttg tgtcagaatt tgaatcaacc    8889
ttacagatac tgggtggcca gaaaatctag tccaagtaat atcctgaaaa atagcaactg    8949
gcaaatacta aaggcagtga agagtttcct ttagatcaga tgataaaaaa aaatcatatg    9009
ttcaatagca ataatcactc acatttttt  tgctgtttag aatttagata attagtagtt    9069
aaacttctat agcttgcgta gctaagatca atggtgatta ttagttgaaa aaataatcaa    9129
atcatcaaac tgaggagact tatacctgcc ataagttctg aaatttcaat gatcctagtc    9189
aatatttact gtatatatag aattaggtcc aaaagatgat acttacaatt aaggatgttg    9249
tattgatcgg ttcataactc aagcttctat ttatcattaa tcaaaagctg gatcattcat    9309
gcatatacct ttgccgcact caacgtagca gctcggagtc ttctttgttc agaagcgagg    9369
aaggagtcaa caaataagta ctgcaatgtt aaacaaaccg acatatcaaa tcccaaatta    9429
agaatgcatg atttattaat acaggaaata tatgatcaag tcccaaaaag tgagtcatgt    9489
tatgtacact cagtcatcaa tttcaataag aatattaact tgctcattgg tatatggatt    9549
tgattatgac ataatttgac aatacattta cagaataaac ttgcagtgct gtgagcatat    9609
gttactaaca tgtaaggacc ttgttttgct ctgttcaata ctcatgttga tcttgatctg    9669
tgtccacata tacctaaatg aaatgaaatc aagaatgag  gtttgtagga gtggagttgg    9729
tgaattatag ggtagataat gtcggcacaa ccgtttgata agtagtacga gtactttatt    9789
tggcgccacc gcgccagcat cagatgtgtg gcctttgcac tgattgaatc caaagaaaa     9849
aaaaagtcgt tttggtccca cacaattcta cttcatctgc aggatgtaca gaaggttaca    9909
tatctattct gttctatgct ctgtttacat ttatatttat agtactaggt tgaaagggct    9969
cacttggtgg ctgtcattgg ttggctggtg cggtatatta ctaataggtt ttttaatggc   10029
atatatgttc ttaaaataaa ccagaaaagc aaaagatcaa ctatcttagc cacaccaatg   10089
aaatggaata tactgaactg tcacggctaa aattctcttc agtcacctgg cccaactgga   10149
```

-continued

```
gccgtgggct cgtcgtcttt tctaaacatg tactagtatt ttgggggccc acagtgaatt   10209
tggcccaaaa tgctgacagc cgctctacgg ctctacgctg tgcag at  ggg cgg ttc   10265
                                                     Tyr Gly Arg Phe
                                                             140 atg atg cgg ctg aag ctg cca aac ggt gtg acg acg agc gag cag acg   10313
Met Met Arg Leu Lys Leu Pro Asn Gly Val Thr Thr Ser Glu Gln Thr
            145                 150                 155 agg tac ctg gcg agc gtg atc gag gcg tac ggc aag gag ggc tgc gcc   10361
Arg Tyr Leu Ala Ser Val Ile Glu Ala Tyr Gly Lys Glu Gly Cys Ala
        160                 165                 170 gac gtg aca acc cgc cag aac tgg cag atc cgc ggc gtc acg ctc ccc   10409
Asp Val Thr Thr Arg Gln Asn Trp Gln Ile Arg Gly Val Thr Leu Pro
    175                 180                 185 gac gtg ccg gcc atc ctc gac ggg ctc aac gcc gtc ggc ctc acc agc   10457
Asp Val Pro Ala Ile Leu Asp Gly Leu Asn Ala Val Gly Leu Thr Ser
190                 195                 200 ctc cag agc ggc atg gac aac gtc cgc aac ccc gtc ggc aac ccg ctc   10505
Leu Gln Ser Gly Met Asp Asn Val Arg Asn Pro Val Gly Asn Pro Leu
205                 210                 215                 220 gcc ggc atc gac ccc gac gag atc gtc gac acg cga tcc tac acc aac   10553
Ala Gly Ile Asp Pro Asp Glu Ile Val Asp Thr Arg Ser Tyr Thr Asn
                225                 230                 235 ctc ctc tcc tcc tac atc acc agc aac ttc cag ggc aac ccc acc atc   10601
Leu Leu Ser Ser Tyr Ile Thr Ser Asn Phe Gln Gly Asn Pro Thr Ile
            240                 245                 250 acc aac ct  gtgagtgatc gaatcaaatt gatcatgctc tgtgctgtgc            10649
Thr Asn Leu tgtttcgtgt cgtctctgac gacatgtttg ttgaatttgt tgttgctgcg tgctgttggc   10709 ag g ccg agg aag tgg aac gtg tgc gtg atc ggg tcg cac gat ctg tac   10757
   Pro Arg Lys Trp Asn Val Cys Val Ile Gly Ser His Asp Leu Tyr
           260                 265                 270 gag cac cca cac atc aac gac ctc gcg tac atg ccg gcg gtg aag ggc   10805
Glu His Pro His Ile Asn Asp Leu Ala Tyr Met Pro Ala Val Lys Gly
            275                 280                 285 ggc aag ttc ggg ttc aac ctc ctc gtc ggc ggg ttc ata agc ccc aag   10853
Gly Lys Phe Gly Phe Asn Leu Leu Val Gly Gly Phe Ile Ser Pro Lys
        290                 295                 300 agg tgg gag gag gcg ctg ccg ctc gac gcc tgg gtc ccc ggc gac gac   10901
Arg Trp Glu Glu Ala Leu Pro Leu Asp Ala Trp Val Pro Gly Asp Asp
    305                 310                 315 atc atc ccg gtg tgc aag gcc gtt ctc gag gcg tac cgc gac ctc ggc   10949
Ile Ile Pro Val Cys Lys Ala Val Leu Glu Ala Tyr Arg Asp Leu Gly
320                 325                 330 acc agg ggc aac cgc cag aag acc cgc atg atg tgg ctc atc gac gaa   10997
Thr Arg Gly Asn Arg Gln Lys Thr Arg Met Met Trp Leu Ile Asp Glu
335                 340                 345                 350 ctt gtgaaccatt tttttctcca ttcatccacg ccattgactg aattacgtat         11050
Leu gtcccaatgt tcttatcagt taattgcggt gttggcattg cag gga atg gag gct   11105
                                                Gly Met Glu Ala
                                                            355 ttt cgg tcg gag gtg gag aag agg atg ccg aac ggc gtg ctg gag cgc   11153
Phe Arg Ser Glu Val Glu Lys Arg Met Pro Asn Gly Val Leu Glu Arg
            360                 365                 370 gcg gcg ccg gag gac ctc atc gac aag aaa tgg cag agg agg gac tac   11201
Ala Ala Pro Glu Asp Leu Ile Asp Lys Lys Trp Gln Arg Arg Asp Tyr
        375                 380                 385
```

| | | | | | | | | | | | | | | | |
|---|---|---|---|---|---|---|---|---|---|---|---|---|---|---|---|
| ctc | ggc | gtg | cac | ccg | cag | aag | cag | gaa | ggg | atg | tcc | tac | gtc | ggc | ctg |
| Leu | Gly | Val | His | Pro | Gln | Lys | Gln | Glu | Gly | Met | Ser | Tyr | Val | Gly | Leu |
| | | | 390 | | | | 395 | | | | 400 | | | | |

11249

| cac | gtg | ccc | gtc | ggc | cgg | gtg | cag | gcg | gcg | gac | atg | ttc | gag | ctc | gca |
|---|---|---|---|---|---|---|---|---|---|---|---|---|---|---|---|
| His | Val | Pro | Val | Gly | Arg | Val | Gln | Ala | Ala | Asp | Met | Phe | Glu | Leu | Ala |
| 405 | | | | | 410 | | | | | 415 | | | | | |

11297

| cgc | ctc | gcc | gac | gag | tac | ggc | tcc | ggc | gag | ctc | cgc | ctc | acc | gtg | gag |
|---|---|---|---|---|---|---|---|---|---|---|---|---|---|---|---|
| Arg | Leu | Ala | Asp | Glu | Tyr | Gly | Ser | Gly | Glu | Leu | Arg | Leu | Thr | Val | Glu |
| 420 | | | | | 425 | | | | | 430 | | | | | 435 |

11345

| cag | aac | atc | gtg | atc | ccg | aac | gtc | aag | aac | gag | aag | gtg | gag | gcg | ctg |
|---|---|---|---|---|---|---|---|---|---|---|---|---|---|---|---|
| Gln | Asn | Ile | Val | Ile | Pro | Asn | Val | Lys | Asn | Glu | Lys | Val | Glu | Ala | Leu |
| | | | | 440 | | | | | 445 | | | | | 450 | |

11393

| ctc | tcc | gag | ccg | ctg | ctt | cag | aag | ttc | tcc | ccg | cag | ccg | tcg | ctg | ctg |
|---|---|---|---|---|---|---|---|---|---|---|---|---|---|---|---|
| Leu | Ser | Glu | Pro | Leu | Leu | Gln | Lys | Phe | Ser | Pro | Gln | Pro | Ser | Leu | Leu |
| | | | | 455 | | | | | 460 | | | | | 465 | |

11441

| ctc | aag | ggc | ctc | gtc | gcg | tgc | acc | ggc | aac | cag | ttc | tgc | ggc | cag | gcc |
|---|---|---|---|---|---|---|---|---|---|---|---|---|---|---|---|
| Leu | Lys | Gly | Leu | Val | Ala | Cys | Thr | Gly | Asn | Gln | Phe | Cys | Gly | Gln | Ala |
| | | | 470 | | | | | 475 | | | | | 480 | | |

11489

| atc | atc | gag | acg | aag | cag | cgg | gcg | ctg | ctg | gtg | acg | tcg | cag | gtg | gag |
|---|---|---|---|---|---|---|---|---|---|---|---|---|---|---|---|
| Ile | Ile | Glu | Thr | Lys | Gln | Arg | Ala | Leu | Leu | Val | Thr | Ser | Gln | Val | Glu |
| 485 | | | | | 490 | | | | | 495 | | | | | |

11537

| aag | ctc | gtg | tcg | gtg | ccc | cgg | gcg | gtg | cgg | atg | cac | tgg | acc | ggc | tgc |
|---|---|---|---|---|---|---|---|---|---|---|---|---|---|---|---|
| Lys | Leu | Val | Ser | Val | Pro | Arg | Ala | Val | Arg | Met | His | Trp | Thr | Gly | Cys |
| 500 | | | | | 505 | | | | | 510 | | | | | 515 |

11585

| ccc | aac | agc | tgc | ggc | cag | gtg | cag | gtc | gcc | gac | atc | ggc | ttc | atg | ggc |
|---|---|---|---|---|---|---|---|---|---|---|---|---|---|---|---|
| Pro | Asn | Ser | Cys | Gly | Gln | Val | Gln | Val | Ala | Asp | Ile | Gly | Phe | Met | Gly |
| | | | | 520 | | | | | 525 | | | | | 530 | |

11633

| tgc | ctc | acc | aag | gac | agc | gcc | ggc | aag | atc | gtt | gag | gcg | gcc | gac | atc |
|---|---|---|---|---|---|---|---|---|---|---|---|---|---|---|---|
| Cys | Leu | Thr | Lys | Asp | Ser | Ala | Gly | Lys | Ile | Val | Glu | Ala | Ala | Asp | Ile |
| | | | 535 | | | | | 540 | | | | | 545 | | |

11681

| ttc | gtc | ggc | ggc | cgc | gtc | ggc | agc | gac | tcg | cac | ctc | gcc | ggc | gcg | tac |
|---|---|---|---|---|---|---|---|---|---|---|---|---|---|---|---|
| Phe | Val | Gly | Gly | Arg | Val | Gly | Ser | Asp | Ser | His | Leu | Ala | Gly | Ala | Tyr |
| | | 550 | | | | | 555 | | | | | 560 | | | |

11729

| aag | aag | tcc | gtg | ccg | tgc | gac | gag | ctg | gcg | ccg | atc | gtc | gcc | gac | atc |
|---|---|---|---|---|---|---|---|---|---|---|---|---|---|---|---|
| Lys | Lys | Ser | Val | Pro | Cys | Asp | Glu | Leu | Ala | Pro | Ile | Val | Ala | Asp | Ile |
| 565 | | | | | 570 | | | | | 575 | | | | | |

11777

| ctg | gtc | gag | cgg | ttc | ggg | gcc | gtg | cgg | agg | gag | agg | gag | gag | gac | gag |
|---|---|---|---|---|---|---|---|---|---|---|---|---|---|---|---|
| Leu | Val | Glu | Arg | Phe | Gly | Ala | Val | Arg | Arg | Glu | Arg | Glu | Glu | Asp | Glu |
| 580 | | | | | 585 | | | | | 590 | | | | | 595 |

11825

| gag | tag | gaacacagac | tggggtgttt | tgcttgctcc | ggtgatctct | cgccgtcctt |
|---|---|---|---|---|---|---|
| Glu | | | | | | |

11825 gag tag gaacacagac tggggtgttt tgcttgctcc ggtgatctct cgccgtcctt    11881
Glu gtaaagtaga cgacaatatg ccttcgccca tggcacgctt gtactgtcac gttttggttt    11941
gatcttgtag cccaaaagtt gtgttcattc tcgttacagt cttacagagg atgattgatt    12001
gataaataaa gaagaaacag attctgcaac tgttcatcgc tgttcctaaa tctgatttag    12061
cgaaagtatc ttgcctgacc tgtcccaatc gcagtgctaa aaccatataa tcttgcaagc    12121
aaatgaaatt gaaagagttc aatgcaacca ctaacagtct aacaacatga taaggcct      12179

<210> SEQ ID NO 5
<211> LENGTH: 2508
<212> TYPE: DNA
<213> ORGANISM: Oryza sativa
<220> FEATURE:
<221> NAME/KEY: CDS
<222> LOCATION: (519)..(2309)
<223> OTHER INFORMATION:

<400> SEQUENCE: 5
tatcgaacct tatctccttc tctctcgtcg ctttctgcgt ctccccgtct ctccttcgcc    60

-continued

```
aacagccgag aagaggcaga gagagcgccg ccccccgtcc ctctctctcc ctctcgtcct    120
cgcccccatc cctctcgtct ttcccttgcc ggcagcagag gaggcggcag cgacggcttc    180
agctgctccc acgggccgga tcgggcagtg gcggtggcgt cggcggcttc cgctggcgaa    240
tccggcgggt ggatacaaat cagtgttccg ataggtaaaa ccctgctctc agcatctgcc    300
cttttgaatt cgccaagagc cagcatctgc ccttttgaat tcgccaaggg ccagcatctg    360
cccatttgat tttgaattcg ccaagagcca gcaacagcgc cccgcgccc cctccctcct     420 ccgcaataaa cagccacacg cgccgccccc atgtccaccc tcatcgccac agcgcaccac    480
caccaccacc accaccacca ccaccaccgt ctccagcc atg gcc tcc tcc gcc tcc   536
                                         Met Ala Ser Ser Ala Ser
                                          1               5
```

| | | | | | | | | | | | | | | | | |
|---|---|---|---|---|---|---|---|---|---|---|---|---|---|---|---|---|
| ctg | cag | cgc | ttc | ctc | ccc | ccg | tac | ccc | cac | gcg | gca | gca | tcc | cgc | tgc | 584 |
| Leu | Gln | Arg | Phe | Leu | Pro | Pro | Tyr | Pro | His | Ala | Ala | Ala | Ser | Arg | Cys | |
| | | 10 | | | | 15 | | | | 20 | | | | | | |

| | | | | | | | | | | | | | | | | |
|---|---|---|---|---|---|---|---|---|---|---|---|---|---|---|---|---|
| cgc | cct | ccc | ggc | gtc | cgc | gcc | cgc | ccc | gtg | cag | tcg | tcg | acg | gtg | tcc | 632 |
| Arg | Pro | Pro | Gly | Val | Arg | Ala | Arg | Pro | Val | Gln | Ser | Ser | Thr | Val | Ser | |
| | 25 | | | | 30 | | | | | 35 | | | | | | |

| | | | | | | | | | | | | | | | | |
|---|---|---|---|---|---|---|---|---|---|---|---|---|---|---|---|---|
| gca | ccg | tcc | tcc | tcg | act | ccg | gcg | gcg | gac | gag | gcc | gtg | tcg | gcg | gag | 680 |
| Ala | Pro | Ser | Ser | Ser | Thr | Pro | Ala | Ala | Asp | Glu | Ala | Val | Ser | Ala | Glu | |
| 40 | | | | | 45 | | | | | 50 | | | | | | |

| | | | | | | | | | | | | | | | | |
|---|---|---|---|---|---|---|---|---|---|---|---|---|---|---|---|---|
| cgg | ctg | gag | ccg | cgg | gtg | gag | cag | cgg | gag | ggc | cgg | tac | tgg | gtg | ctc | 728 |
| Arg | Leu | Glu | Pro | Arg | Val | Glu | Gln | Arg | Glu | Gly | Arg | Tyr | Trp | Val | Leu | |
| 55 | | | | 60 | | | | | 65 | | | | | 70 | | |

| | | | | | | | | | | | | | | | | |
|---|---|---|---|---|---|---|---|---|---|---|---|---|---|---|---|---|
| aag | gag | aag | tac | cgg | acg | ggg | ctg | aac | ccg | cag | gag | aag | gtg | aag | ctg | 776 |
| Lys | Glu | Lys | Tyr | Arg | Thr | Gly | Leu | Asn | Pro | Gln | Glu | Lys | Val | Lys | Leu | |
| | | | 75 | | | | | 80 | | | | | 85 | | | |

| | | | | | | | | | | | | | | | | |
|---|---|---|---|---|---|---|---|---|---|---|---|---|---|---|---|---|
| ggg | aag | gag | ccc | atg | tca | ttg | ttc | atg | gag | ggc | ggc | atc | aag | gag | ctc | 824 |
| Gly | Lys | Glu | Pro | Met | Ser | Leu | Phe | Met | Glu | Gly | Gly | Ile | Lys | Glu | Leu | |
| | | | 90 | | | | | 95 | | | | | 100 | | | |

| | | | | | | | | | | | | | | | | |
|---|---|---|---|---|---|---|---|---|---|---|---|---|---|---|---|---|
| gcc | aag | atg | ccc | atg | gag | gag | atc | gag | gcc | gac | aag | ctc | tcc | aag | gag | 872 |
| Ala | Lys | Met | Pro | Met | Glu | Glu | Ile | Glu | Ala | Asp | Lys | Leu | Ser | Lys | Glu | |
| | | 105 | | | | | 110 | | | | | 115 | | | | |

| | | | | | | | | | | | | | | | | |
|---|---|---|---|---|---|---|---|---|---|---|---|---|---|---|---|---|
| gac | atc | gac | gtg | cgg | ctc | aag | tgg | ctc | ggc | ctc | ttc | cac | cgc | cgc | aag | 920 |
| Asp | Ile | Asp | Val | Arg | Leu | Lys | Trp | Leu | Gly | Leu | Phe | His | Arg | Arg | Lys | |
| 120 | | | | | 125 | | | | | 130 | | | | | | |

| | | | | | | | | | | | | | | | | |
|---|---|---|---|---|---|---|---|---|---|---|---|---|---|---|---|---|
| cat | cag | tat | ggg | cgg | ttc | atg | atg | cgg | ctg | aag | ctg | cca | aac | ggt | gtg | 968 |
| His | Gln | Tyr | Gly | Arg | Phe | Met | Met | Arg | Leu | Lys | Leu | Pro | Asn | Gly | Val | |
| 135 | | | | 140 | | | | | 145 | | | | | 150 | | |

| | | | | | | | | | | | | | | | | |
|---|---|---|---|---|---|---|---|---|---|---|---|---|---|---|---|---|
| acg | acg | agc | gag | cag | acg | agg | tac | ctg | gcg | agc | gtg | atc | gag | gcg | tac | 1016 |
| Thr | Thr | Ser | Glu | Gln | Thr | Arg | Tyr | Leu | Ala | Ser | Val | Ile | Glu | Ala | Tyr | |
| | | | | 155 | | | | | 160 | | | | | 165 | | |

| | | | | | | | | | | | | | | | | |
|---|---|---|---|---|---|---|---|---|---|---|---|---|---|---|---|---|
| ggc | aag | gag | ggc | tgc | gcc | gac | gtg | aca | acc | cgc | cag | aac | tgg | cag | atc | 1064 |
| Gly | Lys | Glu | Gly | Cys | Ala | Asp | Val | Thr | Thr | Arg | Gln | Asn | Trp | Gln | Ile | |
| | | | 170 | | | | | 175 | | | | | 180 | | | |

| | | | | | | | | | | | | | | | | |
|---|---|---|---|---|---|---|---|---|---|---|---|---|---|---|---|---|
| cgc | ggc | gtc | acg | ctc | ccc | gac | gtg | ccg | gcc | atc | ctc | gac | ggg | ctc | aac | 1112 |
| Arg | Gly | Val | Thr | Leu | Pro | Asp | Val | Pro | Ala | Ile | Leu | Asp | Gly | Leu | Asn | |
| | | 185 | | | | | 190 | | | | | 195 | | | | |

| | | | | | | | | | | | | | | | | |
|---|---|---|---|---|---|---|---|---|---|---|---|---|---|---|---|---|
| gcc | gtc | ggc | ctc | acc | agc | ctc | cag | agc | ggc | atg | gac | aac | gtc | cgc | aac | 1160 |
| Ala | Val | Gly | Leu | Thr | Ser | Leu | Gln | Ser | Gly | Met | Asp | Asn | Val | Arg | Asn | |
| | 200 | | | | | 205 | | | | | 210 | | | | | |

| | | | | | | | | | | | | | | | | |
|---|---|---|---|---|---|---|---|---|---|---|---|---|---|---|---|---|
| ccc | gtc | ggc | aac | ccg | ctc | gcc | ggc | atc | gac | ccc | gac | gag | atc | gtc | gac | 1208 |
| Pro | Val | Gly | Asn | Pro | Leu | Ala | Gly | Ile | Asp | Pro | Asp | Glu | Ile | Val | Asp | |
| 215 | | | | | 220 | | | | | 225 | | | | | 230 | |

| | | | | | | | | | | | | | | | | |
|---|---|---|---|---|---|---|---|---|---|---|---|---|---|---|---|---|
| acg | cga | tcc | tac | acc | aac | ctc | ctc | tcc | tcc | tac | atc | acc | agc | aac | ttc | 1256 |
| Thr | Arg | Ser | Tyr | Thr | Asn | Leu | Leu | Ser | Ser | Tyr | Ile | Thr | Ser | Asn | Phe | |
| | | | | 235 | | | | | 240 | | | | | 245 | | |

| | | | | | | | | | | | | | | | | |
|---|---|---|---|---|---|---|---|---|---|---|---|---|---|---|---|---|
| cag | ggc | aac | ccc | acc | atc | acc | aac | ctg | ccg | agg | aag | tgg | aac | gtg | tgc | 1304 |

```
                Gln Gly Asn Pro Thr Ile Thr Asn Leu Pro Arg Lys Trp Asn Val Cys
                            250                 255                 260 gtg atc ggg tcg cac gat ctg tac gag cac cca cac atc aac gac ctc         1352
Val Ile Gly Ser His Asp Leu Tyr Glu His Pro His Ile Asn Asp Leu
            265                 270                 275 gcg tac atg ccg gcg gtg aag ggc ggc aag ttc ggg ttc aac ctc ctc         1400
Ala Tyr Met Pro Ala Val Lys Gly Gly Lys Phe Gly Phe Asn Leu Leu
        280                 285                 290 gtc ggc ggg ttc ata agc ccc aag agg tgg gag gag gcg ctg ccg ctc         1448
Val Gly Gly Phe Ile Ser Pro Lys Arg Trp Glu Glu Ala Leu Pro Leu
295                 300                 305                 310 gac gcc tgg gtc ccc ggc gac gac atc atc ccg gtg tgc aag gcc gtt         1496
Asp Ala Trp Val Pro Gly Asp Asp Ile Ile Pro Val Cys Lys Ala Val
                315                 320                 325 ctc gag gcg tac cgc gac ctc ggc acc agg ggc aac cgc cag aag acc         1544
Leu Glu Ala Tyr Arg Asp Leu Gly Thr Arg Gly Asn Arg Gln Lys Thr
            330                 335                 340 cgc atg atg tgg ctc atc gac gaa ctt gga atg gag gct ttt cgg tcg         1592
Arg Met Met Trp Leu Ile Asp Glu Leu Gly Met Glu Ala Phe Arg Ser
        345                 350                 355 gag gtg gag aag agg atg ccg aac ggc gtg ctg gag cgc gcg gcg ccg         1640
Glu Val Glu Lys Arg Met Pro Asn Gly Val Leu Glu Arg Ala Ala Pro
360                 365                 370 gag gac ctc atc gac aag aaa tgg cag agg agg gac tac ctc ggc gtg         1688
Glu Asp Leu Ile Asp Lys Lys Trp Gln Arg Arg Asp Tyr Leu Gly Val
375                 380                 385                 390 cac ccg cag aag cag gaa ggg atg tcc tac gtc ggc ctg cac gtg ccc         1736
His Pro Gln Lys Gln Glu Gly Met Ser Tyr Val Gly Leu His Val Pro
                395                 400                 405 gtc ggc cgg gtg cag gcg gcg gac atg ttc gag ctc gca cgc ctc gcc         1784
Val Gly Arg Val Gln Ala Ala Asp Met Phe Glu Leu Ala Arg Leu Ala
            410                 415                 420 gac gag tac ggc tcc ggc gag ctc cgc ctc acc gtg gag cag aac atc         1832
Asp Glu Tyr Gly Ser Gly Glu Leu Arg Leu Thr Val Glu Gln Asn Ile
        425                 430                 435 gtg atc ccg aac gtc aag aac gag aag gtg gag gcg ctg ctc tcc gag         1880
Val Ile Pro Asn Val Lys Asn Glu Lys Val Glu Ala Leu Leu Ser Glu
440                 445                 450 ccg ctg ctt cag aag ttc tcc ccg cag ccg tcg ctg ctc aag ggc             1928
Pro Leu Leu Gln Lys Phe Ser Pro Gln Pro Ser Leu Leu Lys Gly
455                 460                 465                 470 ctc gtc gcg tgc acc ggc aac cag ttc tgc ggc cag gcc atc atc gag         1976
Leu Val Ala Cys Thr Gly Asn Gln Phe Cys Gly Gln Ala Ile Ile Glu
                475                 480                 485 acg aag cag cgg gcg ctg ctg gtg acg tcg cag gtg gag aag ctc gtg         2024
Thr Lys Gln Arg Ala Leu Leu Val Thr Ser Gln Val Glu Lys Leu Val
            490                 495                 500 tcg gtg ccc cgg gcg gtg cgg atg cac tgg acc ggc tgc ccc aac agc         2072
Ser Val Pro Arg Ala Val Arg Met His Trp Thr Gly Cys Pro Asn Ser
        505                 510                 515 tgc ggc cag gtg cag gtc gcc gac atc ggc ttc atg ggc tgc ctc acc         2120
Cys Gly Gln Val Gln Val Ala Asp Ile Gly Phe Met Gly Cys Leu Thr
520                 525                 530 aag gac agc gcc ggc aag atc gtt gag gcg gcc gac atc ttc gtc ggc         2168
Lys Asp Ser Ala Gly Lys Ile Val Glu Ala Ala Asp Ile Phe Val Gly
535                 540                 545                 550 ggc cgc gtc ggc agc gac tcg cac ctc gcc ggc gcg tac aag aag tcc         2216
Gly Arg Val Gly Ser Asp Ser His Leu Ala Gly Ala Tyr Lys Lys Ser
                555                 560                 565
```

```
gtg ccg tgc gac gag ctg gcg ccg atc gtc gcc gac atc ctg gtc gag    2264
Val Pro Cys Asp Glu Leu Ala Pro Ile Val Ala Asp Ile Leu Val Glu
        570                 575                 580 cgg ttc ggg gcc gtg cgg agg gag agg gag gag gac gag gag tag        2309
Arg Phe Gly Ala Val Arg Arg Glu Arg Glu Glu Asp Glu Glu
        585                 590                 595 gaacacagac tggggtgttt tgcttgctcc ggtgatctct cgccgtcctt gtaaagtaga  2369
cgacaatatg ccttcgccca tggcacgctt gtactgtcac gttttggttt gatcttgtag  2429
cccaaaagtt gtgttcattc tcgttacagt cttacagagg atgattgatt gataaataaa  2489
gaagaaacag attctgcaa                                               2508
```

<210> SEQ ID NO 6
<211> LENGTH: 596
<212> TYPE: PRT
<213> ORGANISM: Oryza sativa

<400> SEQUENCE: 6

```
Met Ala Ser Ser Ala Ser Leu Gln Arg Phe Leu Pro Pro Tyr Pro His
1               5                   10                  15

Ala Ala Ala Ser Arg Cys Arg Pro Pro Gly Val Arg Ala Arg Pro Val
            20                  25                  30

Gln Ser Ser Thr Val Ser Ala Pro Ser Ser Thr Pro Ala Ala Asp
        35                  40                  45

Glu Ala Val Ser Ala Glu Arg Leu Glu Pro Arg Val Glu Gln Arg Glu
    50                  55                  60

Gly Arg Tyr Trp Val Leu Lys Glu Lys Tyr Arg Thr Gly Leu Asn Pro
65                  70                  75                  80

Gln Glu Lys Val Lys Leu Gly Lys Glu Pro Met Ser Leu Phe Met Glu
                85                  90                  95

Gly Gly Ile Lys Glu Leu Ala Lys Met Pro Met Glu Glu Ile Glu Ala
            100                 105                 110

Asp Lys Leu Ser Lys Glu Asp Ile Asp Val Arg Leu Lys Trp Leu Gly
        115                 120                 125

Leu Phe His Arg Arg Lys His Gln Tyr Gly Arg Phe Met Met Arg Leu
    130                 135                 140

Lys Leu Pro Asn Gly Val Thr Thr Ser Glu Gln Thr Arg Tyr Leu Ala
145                 150                 155                 160

Ser Val Ile Glu Ala Tyr Gly Lys Glu Gly Cys Ala Asp Val Thr Thr
                165                 170                 175

Arg Gln Asn Trp Gln Ile Arg Gly Val Thr Leu Pro Asp Val Pro Ala
            180                 185                 190

Ile Leu Asp Gly Leu Asn Ala Val Gly Leu Thr Ser Leu Gln Ser Gly
        195                 200                 205

Met Asp Asn Val Arg Asn Pro Val Gly Asn Pro Leu Ala Gly Ile Asp
    210                 215                 220

Pro Asp Glu Ile Val Asp Thr Arg Ser Tyr Thr Asn Leu Leu Ser Ser
225                 230                 235                 240

Tyr Ile Thr Ser Asn Phe Gln Gly Asn Pro Thr Ile Thr Asn Leu Pro
                245                 250                 255

Arg Lys Trp Asn Val Cys Val Ile Gly Ser His Asp Leu Tyr Glu His
            260                 265                 270

Pro His Ile Asn Asp Leu Ala Tyr Met Pro Ala Val Lys Gly Gly Lys
        275                 280                 285

Phe Gly Phe Asn Leu Leu Val Gly Gly Phe Ile Ser Pro Lys Arg Trp
```

-continued

```
            290                 295                 300
Glu Glu Ala Leu Pro Leu Asp Ala Trp Val Pro Gly Asp Asp Ile Ile
305                 310                 315                 320

Pro Val Cys Lys Ala Val Leu Glu Ala Tyr Arg Asp Leu Gly Thr Arg
                325                 330                 335

Gly Asn Arg Gln Lys Thr Arg Met Met Trp Leu Ile Asp Glu Leu Gly
                340                 345                 350

Met Glu Ala Phe Arg Ser Glu Val Glu Lys Arg Met Pro Asn Gly Val
                355                 360                 365

Leu Glu Arg Ala Ala Pro Glu Asp Leu Ile Asp Lys Lys Trp Gln Arg
370                 375                 380

Arg Asp Tyr Leu Gly Val His Pro Gln Lys Gln Glu Gly Met Ser Tyr
385                 390                 395                 400

Val Gly Leu His Val Pro Val Gly Arg Val Gln Ala Ala Asp Met Phe
                405                 410                 415

Glu Leu Ala Arg Leu Ala Asp Glu Tyr Gly Ser Gly Glu Leu Arg Leu
                420                 425                 430

Thr Val Glu Gln Asn Ile Val Ile Pro Asn Val Lys Asn Glu Lys Val
                435                 440                 445

Glu Ala Leu Leu Ser Glu Pro Leu Leu Gln Lys Phe Ser Pro Gln Pro
    450                 455                 460

Ser Leu Leu Lys Gly Leu Val Ala Cys Thr Gly Asn Gln Phe Cys
465                 470                 475                 480

Gly Gln Ala Ile Ile Glu Thr Lys Gln Arg Ala Leu Leu Val Thr Ser
                485                 490                 495

Gln Val Glu Lys Leu Val Ser Val Pro Arg Ala Val Arg Met His Trp
                500                 505                 510

Thr Gly Cys Pro Asn Ser Cys Gly Gln Val Gln Val Ala Asp Ile Gly
                515                 520                 525

Phe Met Gly Cys Leu Thr Lys Asp Ser Ala Gly Lys Ile Val Glu Ala
                530                 535                 540

Ala Asp Ile Phe Val Gly Gly Arg Val Gly Ser Asp Ser His Leu Ala
545                 550                 555                 560

Gly Ala Tyr Lys Lys Ser Val Pro Cys Asp Glu Leu Ala Pro Ile Val
                565                 570                 575

Ala Asp Ile Leu Val Glu Arg Phe Gly Ala Val Arg Arg Glu Arg Glu
                580                 585                 590

Glu Asp Glu Glu
        595
```